United States Patent [19]

Petersen

[11] Patent Number: 5,720,285

[45] Date of Patent: Feb. 24, 1998

[54] METHOD AND APPARATUS FOR CONTROLLING ROTATION OF AN ULTRASOUND TRANSDUCER

[75] Inventor: Alan W. Petersen, Cupertino, Calif.

[73] Assignee: Acuson Corporation, Mountain View, Calif.

[21] Appl. No.: 572,693

[22] Filed: Dec. 14, 1995

Related U.S. Application Data

[63] Continuation of Ser. No. 525,492, Sep. 8, 1995.
[51] Int. Cl.$^6$ ..................................................... A61B 8/00
[52] U.S. Cl. ................................. 128/660.1; 128/662.06
[58] Field of Search ........................... 128/660.1, 662.03, 128/662.06

[56] References Cited

U.S. PATENT DOCUMENTS

| | | | |
|---|---|---|---|
| 4,106,492 | 8/1978 | Schuette et al. | 128/660.1 |
| 4,151,834 | 5/1979 | Sato et al. | 128/660.1 |
| 4,579,122 | 4/1986 | Shimizu et al. | 128/660.09 |
| 4,622,501 | 11/1986 | Eventoff et al. | 128/660.09 |

*Primary Examiner*—Francis Jaworski
*Attorney, Agent, or Firm*—Brinks Hofer Gilson & Lione

[57] ABSTRACT

A method and apparatus is provided for controlling rotation of an ultrasound transducer. In accordance with the method of the present invention, a user-operable actuator that is movable over a continuous range of positions and generates a first signal representing the position of the actuator is provided. The method includes the steps of transforming the first signal into a second signal representing a desired velocity. Preferably, the second signal is a nonlinear transform of the first signal. The method further provides for rotating the ultrasound transducer in accordance with the second signal. In accordance with the apparatus of the present invention, a probe having a control housing, an actuator that may be manually positioned within a range of positions, and a transducer housing coupled to the control housing, which transducer housing contains an ultrasound transducer that is rotatably mounted for scanning a plurality of planes in a body, is disclosed. The probe includes apparatus for controlling rotation of the ultrasound transducer. The control apparatus includes a motor, a motor controller coupled to the motor, and a gain block coupled between the actuator and the motor controller. The gain block preferably has a continuous transfer characteristic and produces, for each position of the actuator, a signal representing a desired velocity.

36 Claims, 12 Drawing Sheets

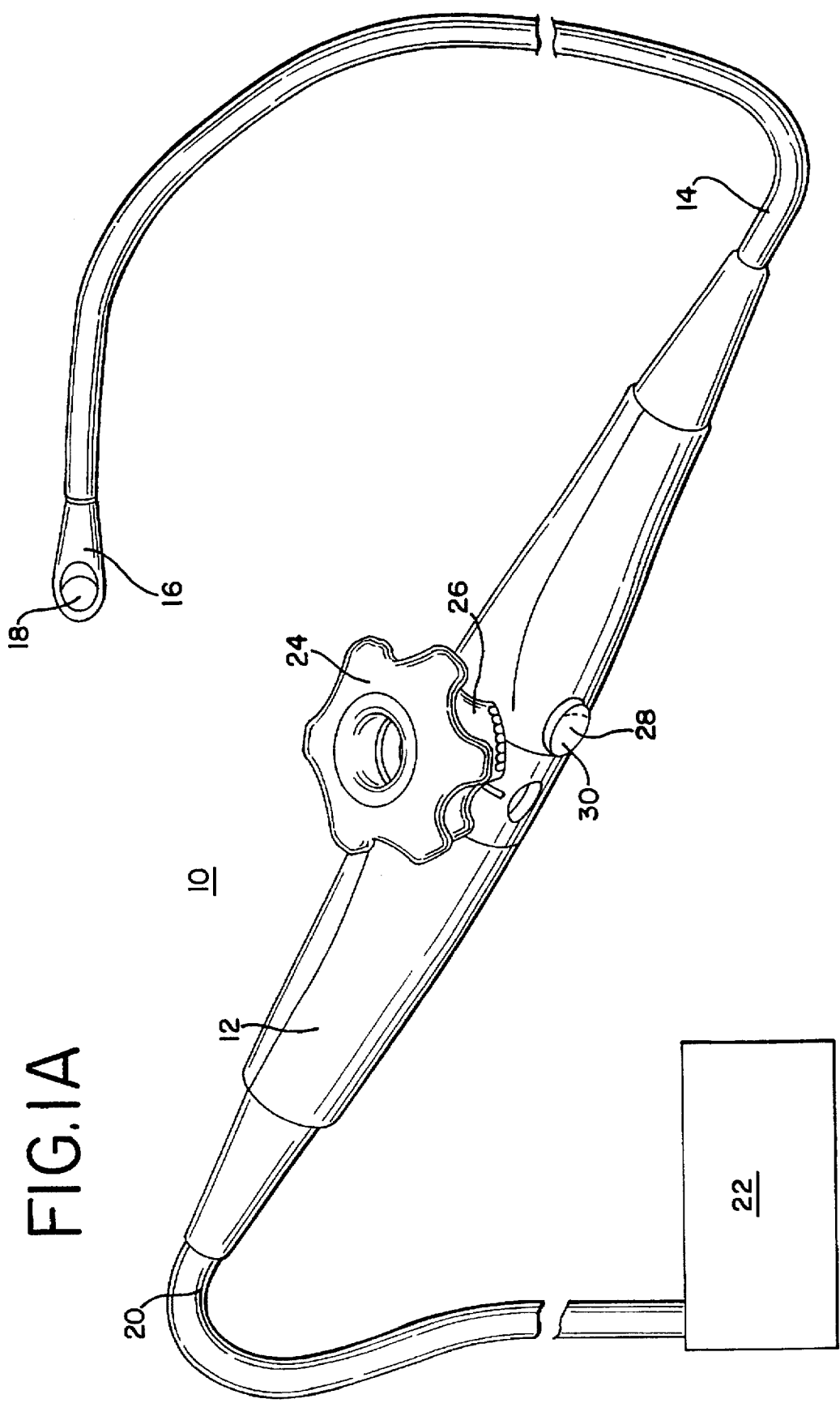

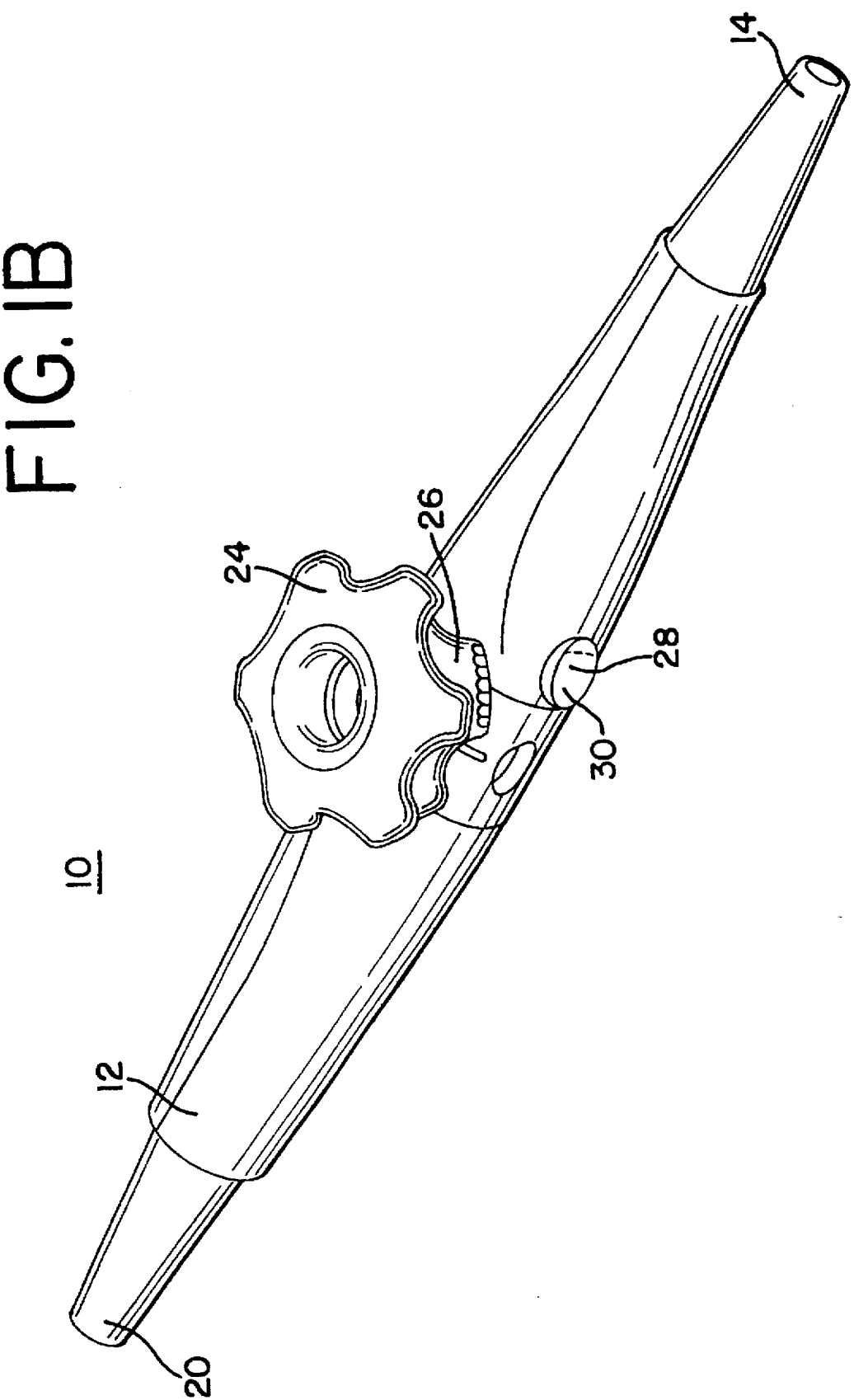

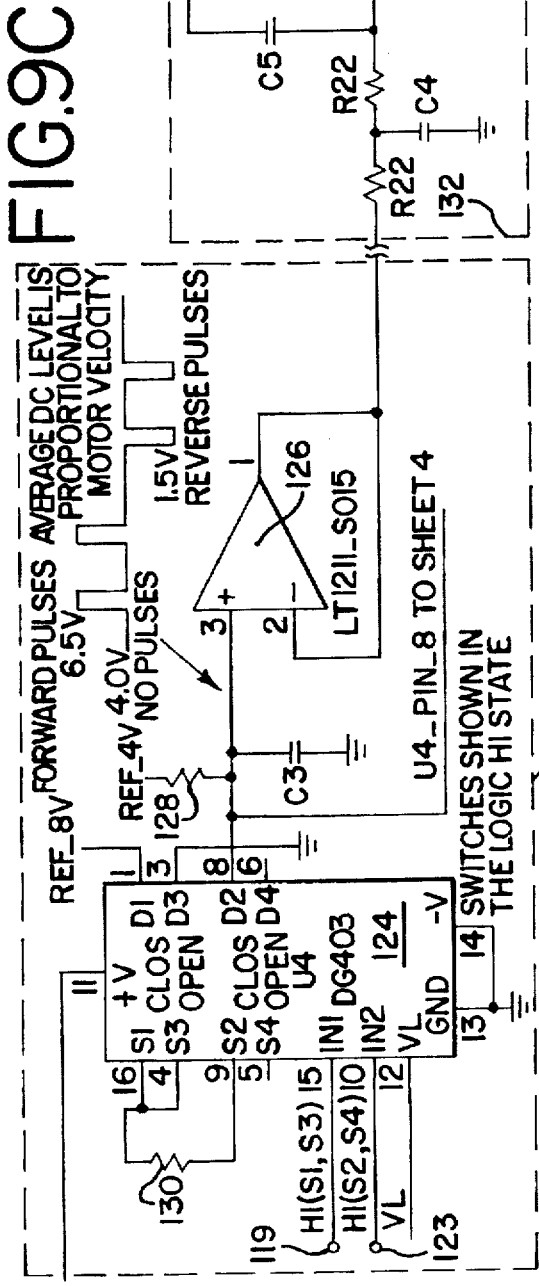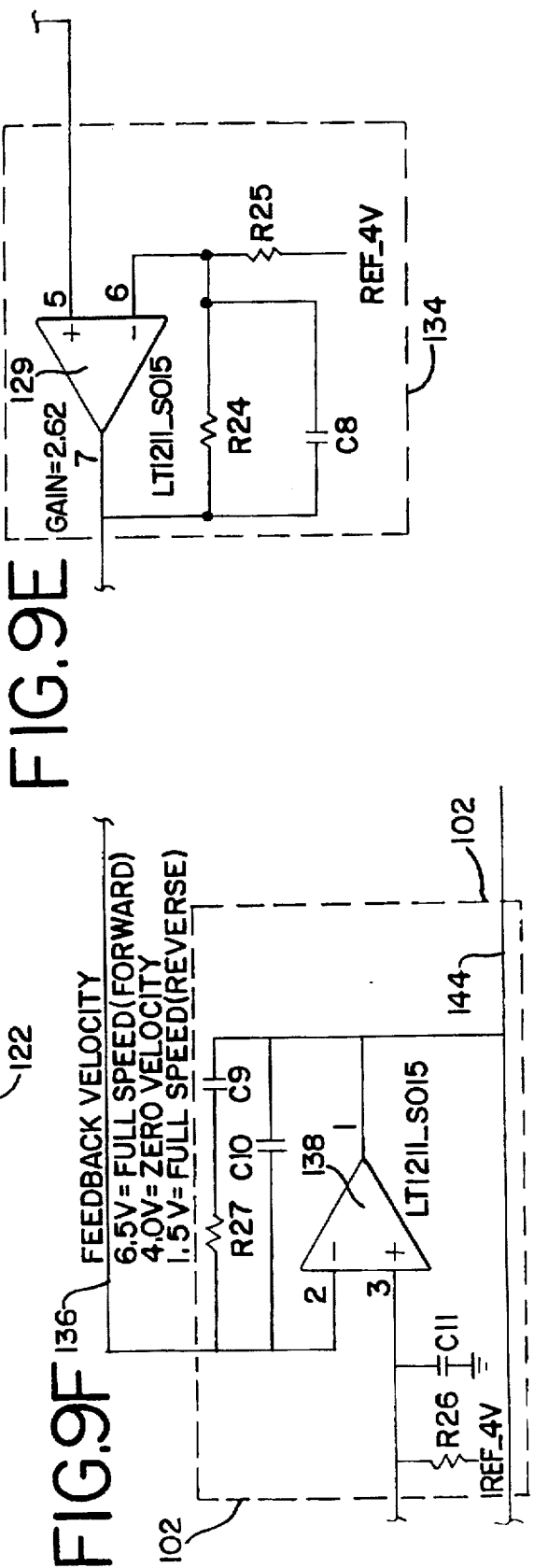

5,720,285

METHOD AND APPARATUS FOR CONTROLLING ROTATION OF AN ULTRASOUND TRANSDUCER

This application is a continuation of U.S. patent application Ser. No. 08/525,492, entitled METHOD AND APPARATUS FOR CONTROLLING ROTATION OF AN ULTRASOUND TRANSDUCER, filed Sep. 8, 1995.

BACKGROUND OF THE INVENTION

The present invention relates to ultrasound imaging systems and, more particularly, to a method and apparatus for controlling rotation of an ultrasound transducer.

The users of medical ultrasound transducer probes, hereinafter referred to as sonographers, can obtain images of a region within a body by properly positioning a probe against the body. In order to obtain images having diagnostic value, the sonographer may have to physically manipulate the position of the probe by sliding, rotating and tilting the probe. One area in particular where this manipulation is more challenging is transesophageal cardiac imaging. During transesophageal cardiac imaging, the sonographer positions a transducer housing at the tip of the probe against the esophagus or stomach of a patient to obtain different fields of view of the heart.

For this application, the transducer housing typically contains a number of acoustic transducer elements, which may be sequentially electrically excited by an ultrasound control and operating system to obtain an image in an object plane that is perpendicular to the transducer housing and the transducer elements.

It has been found desirable to rotate the transducer elements contained within the transducer housing independently from the physical manipulation of the housing itself. In combination with the ability to slide, rotate and tilt the transducer housing, the ability to independently rotate the transducer elements within the housing gives the sonographer the ability to obtain an ultrasound image of any or all object planes orthogonal to the upper surface of the transducer elements at each location to which the housing can be moved.

Devices that allow the sonographer to rotate the transducer elements independently from the transducer housing are known. For example, U.S. Pat. No. 5,402,793 to Gruner et al. shows an ultrasonic transesophageal probe for the imaging and diagnosis of multiple scan planes. The probe includes two buttons that respectively control the clockwise and counter-clockwise rotation of the transducer at the tip of the probe. Each of the buttons is a three-position switch: off, slow rotation and fast rotation. The states of the switches are transmitted to the ultrasound system, interpreted and converted to motor drive signals.

A disadvantage of the Gruner et al. device is that the sonographer is unable to utilize intermediate rotational speeds. A desired position may be overshot when the transducer is rotated in the fast mode, or may take too long to reach when the transducer is rotated in the slow mode. A further disadvantage of the Gruner et al. device is the added complexity, in manufacture and use, of requiring two switches to rotate the transducer. It is desirable to allow the sonographer to quickly, easily and precisely control the rotational position of the transducer anywhere within its typical 0 to 180 degree rotational range.

Accordingly, it would be desirable to have an improved method and apparatus for controlling rotation of the ultrasound transducer.

SUMMARY OF THE INVENTION

In accordance with a first aspect of the present invention, a probe having a control housing, an actuator that may be manually positioned within a range of positions, and a transducer housing coupled to the control housing, which transducer housing contains an ultrasound transducer that is rotatably mounted for scanning a plurality of planes in a body, is provided. The probe includes apparatus for controlling rotation of the ultrasound transducer. The apparatus includes a motor, a motor controller coupled to the motor, and a gain block coupled between the actuator and the motor controller. The gain block has a continuous transfer characteristic and produces, for each position of the actuator, a signal representing a desired velocity.

In accordance with a second aspect of the present invention, an apparatus for controlling rotation of an ultrasound transducer mounted within a distal portion of a probe operatively associated with a bidirectional switch is provided. The apparatus includes a motor mechanically coupled to the transducer and a nonlinear gain block electrically coupled between the switch and the motor. The nonlinear gain block receives a first signal from the switch and transmits a second signal to the motor.

In accordance with a third aspect of the present invention, a method of controlling rotation of an ultrasound transducer that is housed within a distal end of a probe having a user-operable actuator that is movable over a continuous range of positions is provided. The method includes the steps of generating a first signal representing the position of the actuator, transforming the first signal into a second signal representing a desired velocity, and rotating the ultrasound transducer in accordance with the second signal. The second signal is a nonlinear transform of the first signal.

The invention, together with its further objects and attendant advantages, will be understood by reference to the following detailed description taken in conjunction with the accompanying drawings.

BRIEF DESCRIPTION OF THE DRAWINGS

FIGS. 1A and 1B are perspective views of an ultrasound probe in accordance with the present invention.

FIGS. 9A and 9B through 9F are a block diagram and an electrical schematics, respectively, of the velocity detector and velocity servo shown in FIG. 7A.

DETAILED DESCRIPTION OF THE PRESENTLY PREFERRED EMBODIMENTS

Figure 2:
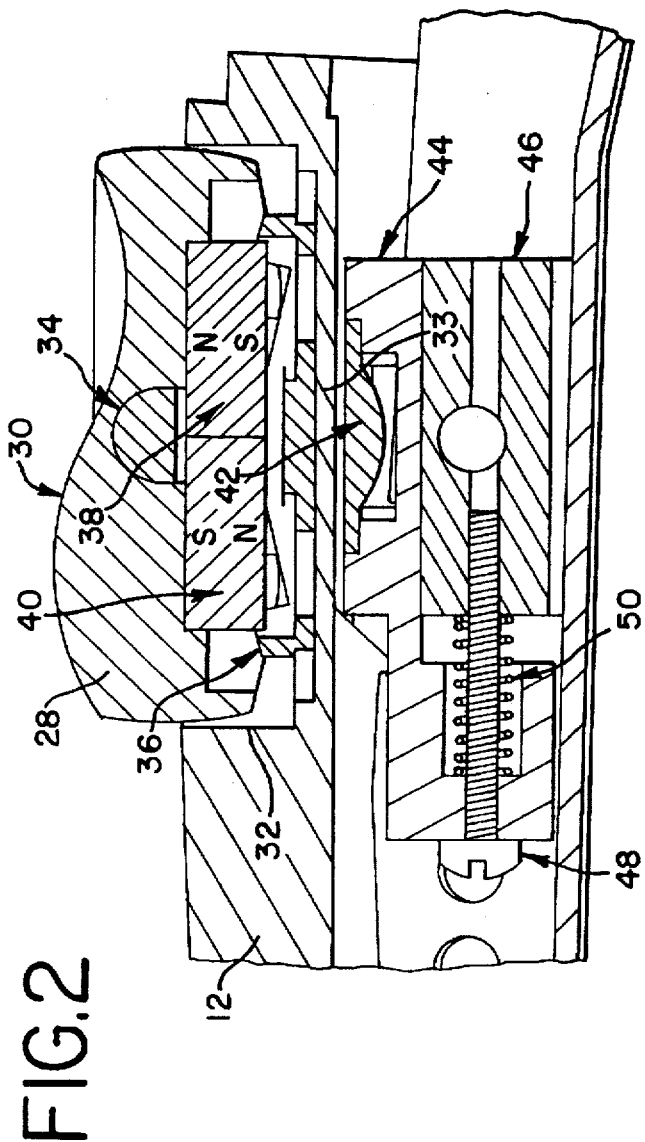
FIG. 2 is a sectional view of an actuator mounted to a control housing of the ultrasound probe shown in FIGS. 1A and 1B.

The invention is described with reference to the drawings in which like elements are referred to by like numerals. FIGS. 1A and 1B are perspective views of an ultrasound probe 10 in accordance with the present invention. The ultrasound probe 10 has a control housing 12 which is designed to fit within the hand of the sonographer.

As shown in FIG. 1A, a gastroscope tube 14 connects the control housing 12 to a transducer housing 16. The transducer housing 16 contains an ultrasound transducer 18. An electrical cable 20 extends from the other end of the control housing 12 to a connector 22, which is designed to interface with an ultrasound control and operating system (not shown).

The control housing 12 contains the major manual controls that are used by the sonographer. The manual controls include control knobs 24 and 26, which are mechanically connected to the distal end of the gastroscope tube 14. As known within the art, the sonographer may cause left to right and forward to back articulation of the transducer housing 16 by rotating the control knobs 24 and 26, respectively. Thus, the control knobs 24 and 26 assist the sonographer in positioning the transducer housing 16 against the esophagus or stomach of a patient.

In accordance with the present invention, the control housing 12 also includes an actuator 28 that may be manipulated by the sonographer to control rotation of the ultrasound transducer 18 within the transducer housing 16. Preferably, the ultrasound transducer 18 is mounted within the transducer housing 16 to rotate between a 0° position, also referred to herein as the home position, and a 180° position. It will be recognized that rotation of the two-dimensional image plane through 180° provides a full 360° of scanning coverage.

As shown in FIGS. 1A and 1B, the actuator 28 is preferably operated by a control button 30 that is located on an outside surface of the control housing 12 in a position where it may be operated by the sonographer's thumb. In FIG. 1A, the control button 30 is shown in its neutral position, whereas the control button 30, as shown in FIG. 1B, is fully tilted in the forward direction.

FIG. 2 is a sectional view of the actuator 28 mounted to the control housing 12 of the ultrasound probe 10 shown in FIGS. 1A and 1B. A preferred embodiment of the actuator 28 is shown. The actuator 28 includes the control button 30, which is located within a recess 32 in the control housing 12. Preferably, the outside surface of the control housing 12 is continuous in the region 33 beneath the control button 30, as shown in FIG. 2. The continuous surface of the control housing 12 provides a hermetic seal between the control button 30 and devices contained within the control housing 12.

The control button 30 is mounted by a pin 34 to a pivot bracket 36 so that the control button 30 may tilt back and forth about its central or balanced position on the pivot bracket 36. The travel limits for the tilting movement of the control button 30 may be defined by the recess 32. In particular, the control button 30 may tilt back and forth within the pivot bracket 36 until the recess 32 interferes with its movement.

The balanced or central position of the control button 30, as shown in FIGS. 1A and 2, is referred to herein as the neutral position. When the control button 30 is in the neutral position, the ultrasound transducer 18 is stationary. On the other hand, when the control button 30 is tilted fully forward, as shown in FIG. 1B, the ultrasound transducer rotates at its maximum speed in the forward direction. Likewise, when the control button 30 is fully tilted in the opposite direction, the ultrasound transducer rotates at its maximum speed in the reverse direction. For purposes of this description, rotation in the forward direction refers to rotation toward the 180° position, while rotation in the reverse direction refers to rotation toward the 0° position.

Preferably, the control button 30 is biased to return to its neutral position when pressure is removed from the control button 30. In this manner, the sonographer may stop rotation of the ultrasound transducer 18 by simply releasing the control button 30. The control button 30 may be biased to return to its neutral position by positioning four springs (not shown) between the control button and the recess 32.

Referring again to FIG. 2, two magnets 38 and 40 are attached to the lower surface of the control button 30. The magnets 38 and 40 are oriented so that their north poles face in opposite directions. As shown in FIG. 2, the first magnet 38 is oriented with its north pole facing upward while the second magnet 40 is oriented with its north pole facing downward.

A hall-effect sensor 42 is positioned within the control housing 12 below the pivot point of the control button 30. Preferably, the hall-effect sensor 42 is mounted within the control housing 12 so that its position may be adjusted. For example, as shown in FIG. 2, the hall-effect sensor 42 may be mounted upon an adjustable bracket 44.

The bracket 44, as shown in FIG. 2, is attached to a shoe 46 by an adjusting screw 48. A spring 50 is positioned around the adjusting screw 48 between the shoe 46 and the bracket 44. The position of the shoe 46 within the control housing 12 is fixed so that the position of the hall-effect sensor 42 may be adjusted using the adjusting screw 48. Alternative schemes for adjustably mounting the hall-effect sensor 42 will be apparent to one of ordinary skill in the art.

The hall-effect sensor 42 is preferably adjustably mounted because it is difficult, if not impossible, to obtain magnets 38 and 40 that have precisely the same strength. The position of the hall-effect sensor 42 may therefore need to be adjusted so that the magnetic null point between the two magnets 38 and 40 coincides with the neutral position of the control button 30.

When arranged as shown in FIG. 2, the hall-effect sensor 42 generates an output electrical signal that is proportional in strength to the position of the control button 30. For example, in a preferred embodiment the hall-effect sensor 42 generates an output of 4.0 volts when the control button 30 is in the neutral position, generates an output of approximately 6.5 volts when the control button 30 is fully displaced in the forward direction, and generates an output of approximately 1.5 volts when the control button 30 is fully displaced in the reverse direction. The control button 30 is continuously displaceable between its forward and reverse travel limits. A hall-effect sensor 42 that is suitable for this application is commercially available from Honeywell Micro Switch of Freeport, Ill., Part No. SS89A1.

The control button 30, pivot bracket 36, magnets 38 and 40, and hall-effect sensor 42 form a bidirectional tilt switch or rocker switch. The switch generates an output electrical signal having a magnitude that corresponds to the position of the control button 30. As shown in FIG. 2, the top surface of the control button 30 may be contoured to improve the sonographer's feel and prevent the thumb from slipping.

Although the structure of the actuator 28 as shown in FIG. 2 is preferred, the actuator 28 may alternatively be implemented by attaching a single magnet to a sliding control button mounted in a recess on the control housing. For this embodiment, two hall-effect sensors are positioned toward opposite longitudinal ends of the recess. As a further alternative, the actuator 28 may be implemented by mounting a control button to the moving arm of a slide potentiometer. In each case, the actuator 28 is capable of generating a signal that varies with the position of the control button 30. The embodiments utilizing hall-effect sensors provide the advantage of allowing a hermetic seal to be located between the control button 30 and the electronics within the control housing 12.

Figure 3:
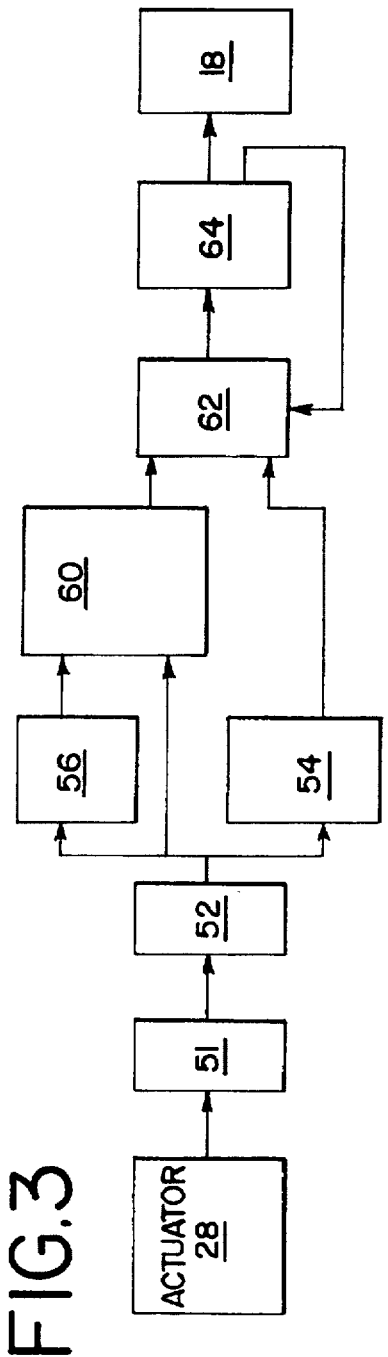
FIG. 3 is a schematic for processing a signal generated by the actuator shown in FIG. 2 to control rotation of an ultrasound transducer.

Referring now to FIG. 3, a schematic for processing a signal generated by the actuator 28, shown in FIG. 2, to control rotation of the ultrasound transducer 18 is shown. The actuator 28 is coupled to an amplifier/limiter 51. The output of the amplifier/limiter 51 is coupled to a low-pass filter 52. The output of the low-pass filter 52 is coupled to a deadband detector 54, a direction sensor 56 and a gain block 60. The output of the gain block 60 is coupled to a motor controller 62. The motor controller 62 is coupled to a motor 64, which rotates the ultrasound transducer 18.

The motor 64 is preferably located within the control housing 12 and coupled to the ultrasound transducer 18 by a flexible drive shaft located within the gastroscope tube 14. In addition, the motor is preferable a DC motor.

Figure 4:
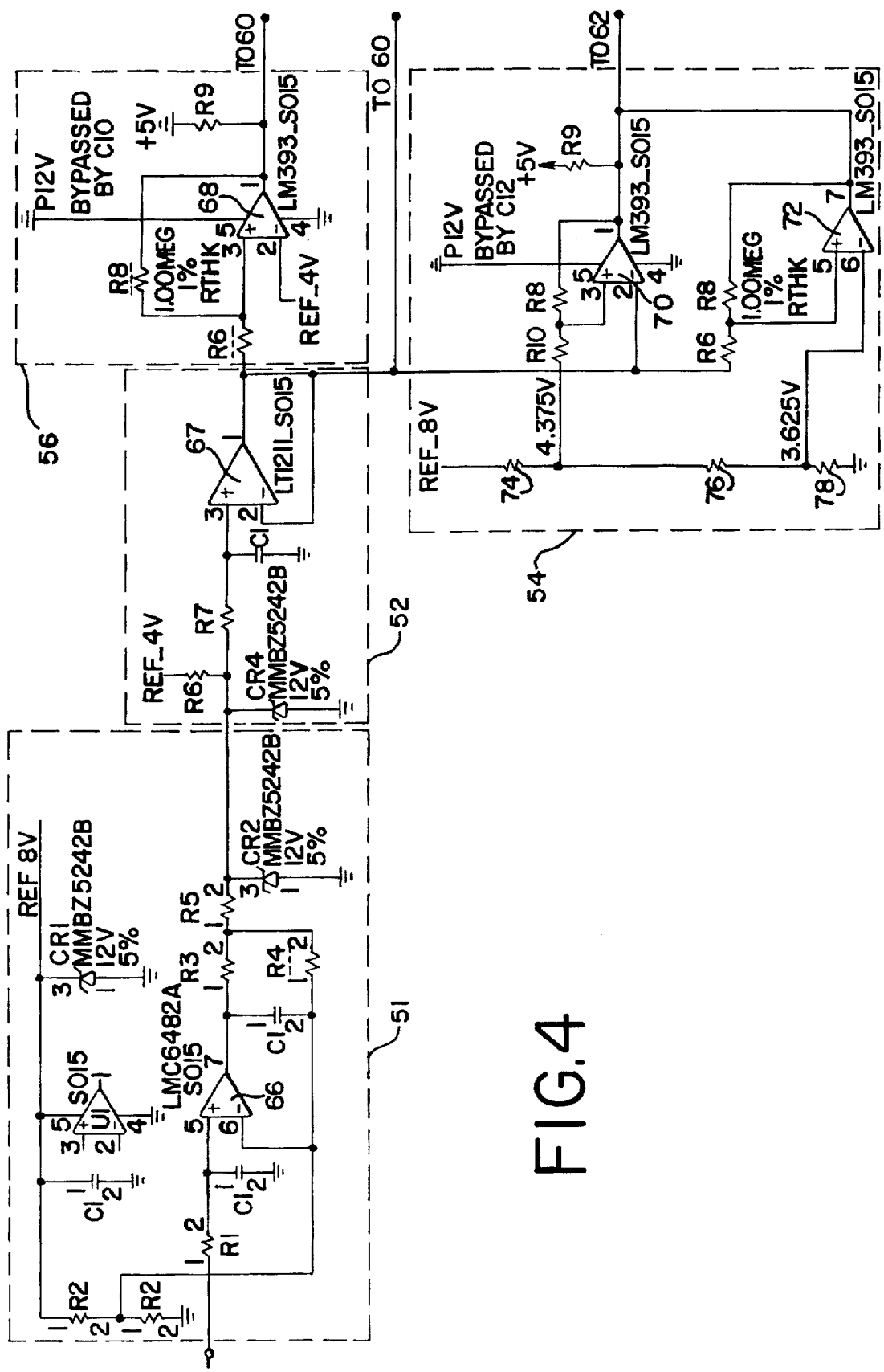
FIG. 4 is an electrical schematic showing preferred embodiments of an amplifier/limiter, a low-pass filter, a direction sensor and a dead band detector from the schematic of FIG. 3.

FIG. 4 is an electrical schematic showing preferred embodiments of the amplifier/limiter 51, the low-pass filter 52, the direction sensor 56 and the deadband detector 54 from the schematic of FIG. 3. Element values for the electrical components shown in FIG. 4 are provided below in Table 1.

As shown in FIG. 4, the output of the hall-effect sensor 42 is provided to the amplifier/limiter 51. In particular, the hall-effect sensor 42 is coupled to the noninverting input of an operational amplifier 66. The operational amplifier 66 amplifies and clips the upper limits of the hall-effect signal to produce an output signal having the following characteristics: the output signal level is 6.6 volts, which corresponds to full speed forward, when the control button 30 of the actuator 28 is displaced to its forward travel limit; the output signal level is 4.0 volts, which corresponds to zero speed, when the control button 30 of the actuator 28 is in the neutral position; and the output signal level is 1.4 volts, which corresponds to full speed reverse, when the control button 30 of the actuator 28 is displaced to its reverse travel limit.

The amplifier/limiter 51 is preferably located on a printed circuit board within the control housing 12. The operational amplifier 66 may be Part No. LMC6482AIM from National Semiconductor in Santa Clara, Calif.

The output of the operational amplifier 66 is coupled to the low-pass filter 52. In the low-pass filter 52, the output of the operational amplifier 66 is coupled to an operational amplifier 67. The low-pass filter 52 removes high frequency interference from the output of the amplifier/limiter 51, such as interference that may be caused by electronic surgical knives or other electronic devices operated within the vicinity of the ultrasound probe 10. For values of the resistor R7 and the capacitor C1 as given in Table 1, the low-pass filter 52 has a cut-off frequency of 16 Hz. The operational amplifier 67 is preferably Part No. LT1211CS8 from Linear Technology of Milpitas, Calif.

As shown in FIG. 4, the direction sensor 56 may be implemented by providing the output of the operational amplifier 67 to the noninverting input of a comparator 68. A 4 volt reference is coupled to the inverting input of the comparator 68. Accordingly, the output of the comparator 68 is a logic high-level signal when the control button 30 is unbalanced in the forward direction, i.e., the signal level of the output of the amplifier 66 is greater than 4 volts. On the other hand, the output of the comparator 68 is a logic low level signal when the control button 30 is unbalanced in the reverse direction, i.e., the signal level of the output of the amplifier 66 is less than 4 volts. As used herein, "forward" direction refers to that displacement of the control button 30 which causes rotation of the ultrasound transducer 18 toward its 180 degree position, and "reverse" direction refers to that displacement of the control button 30 which causes rotation of the ultrasound transducer 18 toward its zero degree position.

The deadband detector 54, shown in FIGS. 3 and 4, ensures that the motor 64 is off when the control button 30 is in its neutral position or only slightly out of balance. Preferably, the deadband detector 54 causes the motor 64 to remain off when the control button 30 is within approximately ±14% of its neutral position. When percentages are used herein to describe the position of the control button 30, the following convention is used: 0% is the neutral position, +100% is the maximum displacement in the forward direction, and −100% is the maximum displacement in the reverse direction. The inventor has found that a deadband improves the sonographer's "feel" for manual velocity control. In addition, the ±14% range provides some tolerance for the ability of the springs to return the control button 30 to its neutral position.

To implement the deadband detector 54, the hall-effect signal is coupled to two voltage comparators 70 and 72 in parallel. The upper and lower thresholds of the comparators 70 and 72 are set by resistors 74, 76 and 78 to produce the approximately ±14% deadband. For resistors 74, 76 and 78 having the values shown in Table 1, the output of the parallel comparators 70 and 72 is a logic low-level signal when the hall-effect signal is either greater than 4.375 volts or less than 3.625 volts. The output of the comparators 70 and 72 is a logic high-level signal when the hall-effect signal is between 3.625 volts and 4.375 volts.

TABLE 1

| | |
|---|---|
| R1 = 4.22 kΩ | R8 = 1.00 MΩ |
| R2 = 21.5 kΩ | R9 = 1.00 kΩ |
| R3 = 100Ω | R10 = 6.81 kΩ |
| R4 = 6.19 kΩ | resistor 74 = 4.99 kΩ |
| R5 = 4.64 kΩ | resistor 76 = 1.10 kΩ |
| R6 = 10 kΩ | resistor 78 = 4.99 kΩ |
| R7 = 100 kΩ | C1 = 0.1 μF |

Referring again to FIG. 3, the motor controller 62 maintains the motor 64 in an off state until the signal from the deadband detector 54 goes low. If the output signal of the deadband detector 54 is a logic low-level signal, then the motor controller 62 obtains the desired motor velocity signal from the low-pass filter 52 via the gain block 60. As described above, the output of the deadband detector 54 goes low when the displacement of the control button 30, in either the forward or reverse direction, exceeds approximately 14%.

Figure 5:
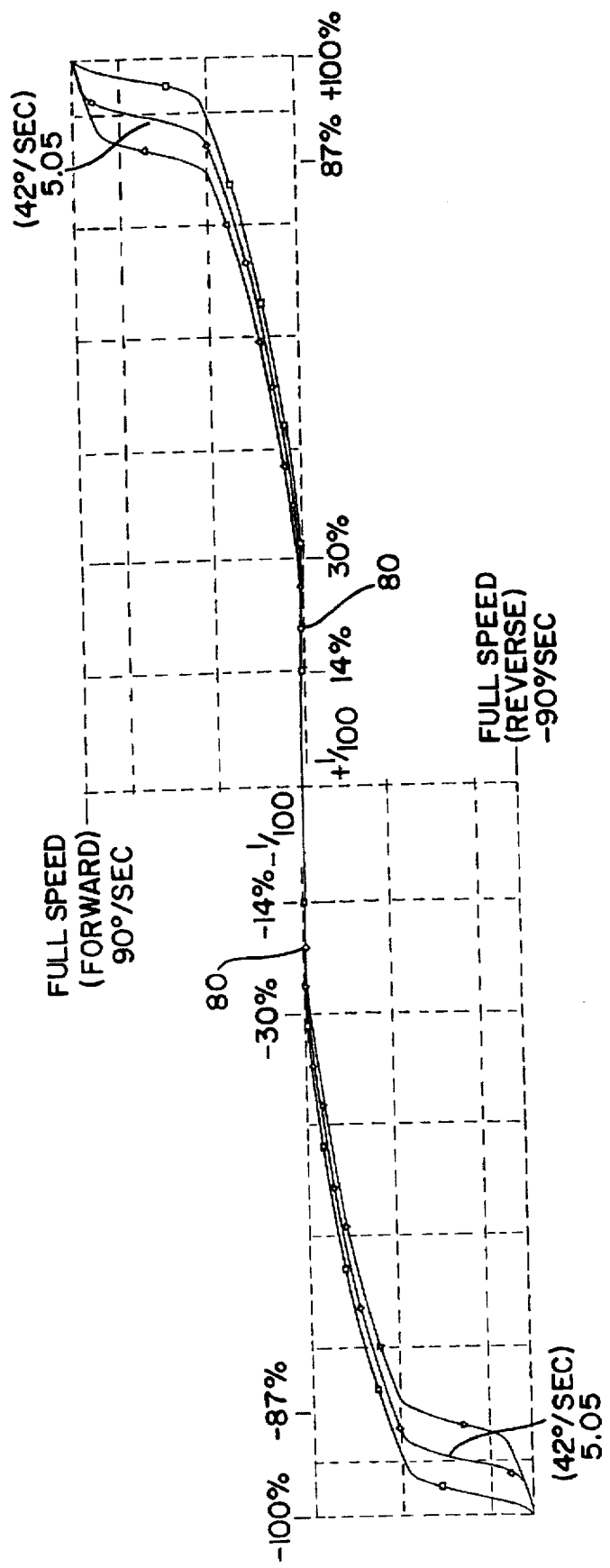
FIG. 5 is a graph of a preferred transfer characteristic for the gain block shown in FIG. 3.

FIG. 5 is a graph of a preferred transfer characteristic 61 for the gain block 60 shown in FIG. 3. The hall-effect sensor 42 produces, at the output of the low-pass filter 52, a signal that is linearly related to the position of the control button 30. With the understanding that the motor is to remain in the off state until the control button 30 is displaced, either in the forward or reverse direction, by more than approximately 14%, the remaining 14% to 100% displacement of the control button 30, in each direction, is mapped by the gain block 60 into a corresponding continuous range of rotational speeds.

Preferably, the continuous range of rotational speeds is broad, such as a range spanning 1/100th full speed to full speed, as shown in FIG. 5. For example, the embodiment described herein has a full speed of 90° per second. Accordingly, 1/100th full speed corresponds to 0.9° per second. Movement at low speeds, such as 0.9° per second, allows the sonographer to precisely position the ultrasound transducer 18 under manual control. At this speed, the sonographer may rotate the ultrasound transducer 18 one degree at a time. Movement at high speeds, on the other hand, allows the sonographer to quickly rotate the ultrasound transducer 18 in large increments, such as when switching between longitudinal and transverse views.

The mapping of control button 30 displacement into the continuous range of rotational speeds is preferably nonlinear. That is, for control button 30 positions within the approximately 14% to 100% range in each direction, the rate of change of rotational speed with respect to displacement of the control button 30 is not constant. In the preferred embodiment, the transfer characteristic 61 of the gain block 60 favors the slower speeds. The majority of the 14% to 100% range is dedicated to slow and moderate speeds, as shown in FIG. 5, for precise manual position control. This means that, in general, the rate of change of rotational speed is lower when the control button 30 is nearer to its balanced or neutral position than when the control button 30 approaches the limits of its range of displacement.

In FIG. 5, the transfer characteristic 61 of a preferred nonlinear gain block 60 is plotted with the gain block output on the vertical axis and the gain block input on the horizontal axis. The gain block 60 transforms an input representing the position of the control button 30 into an output representing the desired velocity. The gain block output, which is coupled to the motor controller 62, corresponds to the desired velocity of the ultrasound transducer 18. The gain block input, which is provided by the low-pass filter 52, corresponds to the percentage of displacement of the control button 30. Preferably, the transfer characteristic 61 of the gain block 60 is continuous as the motor speed increases from 1/100th speed to full speed, as shown in FIG. 5. As used herein, a "continuous" transfer characteristic is one having finite slope over a range of motor speeds.

As shown in FIG. 5, the transfer characteristic 61 includes two flat areas 80, which correspond to displacement of the control button 30 within the range of approximately the neutral position (0%) to approximately 30%, and the neutral position (0%) to approximately −30%. When the control button 30 is positioned within the positive portion of this range, the gain block output is fixed at 1/100th full speed in the forward direction. Similarly, when the control button 30 is positioned within the 0 to −30% portion of this range, the gain block is fixed at 1/100th full speed in the reverse direction. The flat areas 80 are desirable because they allow the sonographer to displace the control button 30 to a range of positions beyond the ±14% deadband zone, while remaining at the slowest speed. Accordingly, the flat areas 80 provided by the gain block 60 provide the advantage of improving the sonographer's feel of control at slow speeds.

Between approximately 30% and 87% of full displacement of the control button 30 in each direction, the transfer characteristic 61 is approximately linear. When the control button 30 is displaced beyond approximately 87% in each direction, the output of the gain block quickly increases to full speed.

Figure 6A:
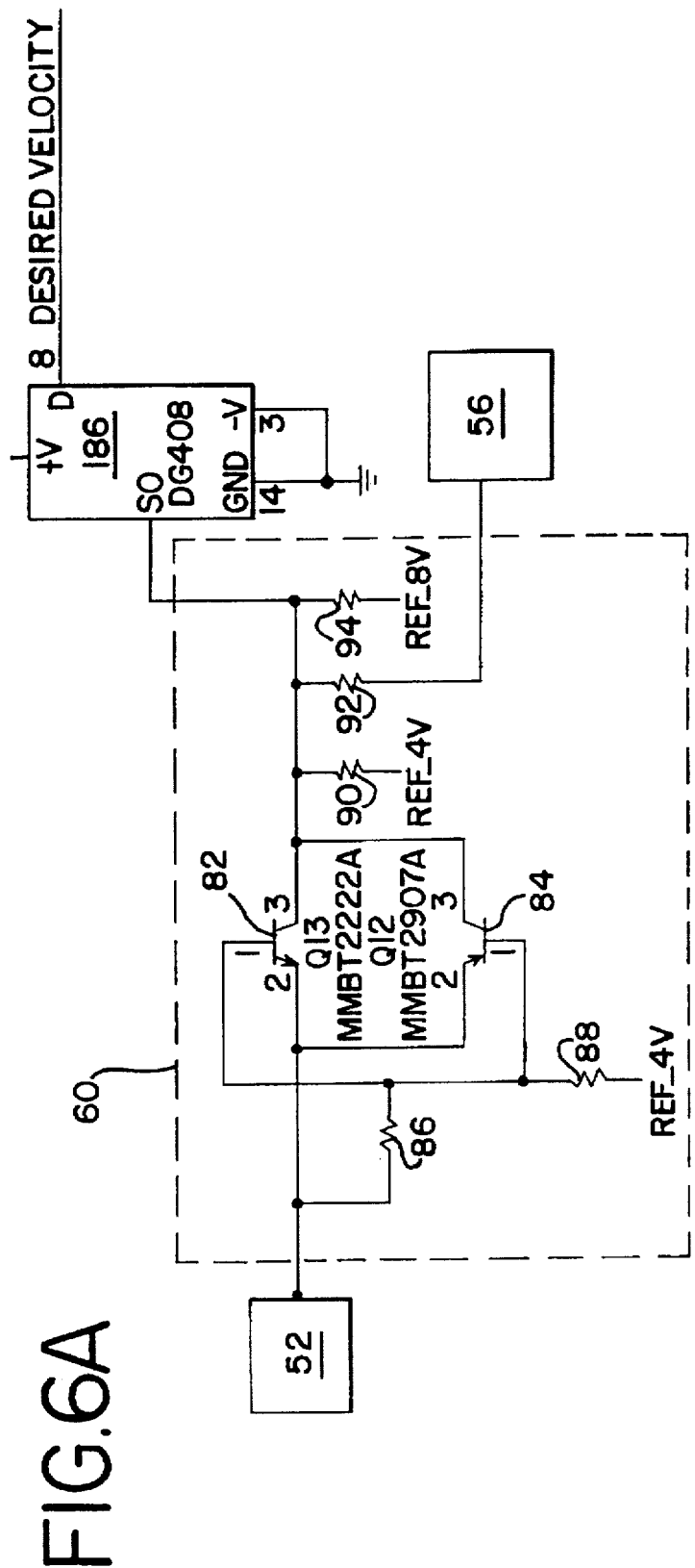
FIGS. 6A and 6B are electrical schematics for producing the transfer characteristic shown in FIG. 5.
Figure 6B:
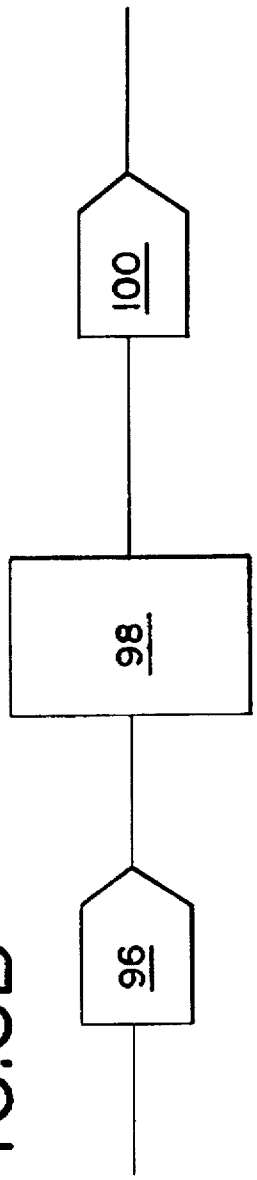

FIGS. 6A and 6B are electrical schematics for producing the transfer characteristic shown in FIG. 5. In FIG. 6A, the output of the low-pass filter 52 is coupled to the emitters of transistors 82 and 84. The output of the low-pass filter 52 is also coupled through resistor 86 to the base of transistors 82 and 84. A 4 volt DC reference voltage is applied to the base of transistors 82 and 84 through a resistor 88. The collectors of the transistors 82 and 84 are coupled. The resistor 90 couples the collectors to a 4 volt DC reference voltage. The resistor 92 couples the collectors to the output of the direction sensor 56, which is shown in FIGS. 3 and 4. Finally, a resistor 94 couples the collector to an 8 volt DC reference voltage.

The transistor 82 is an NPN bipolar junction transistor, such as Part No. MMBT2222A manufactured by Motorola of Phoenix, Ariz. The transistor 84 is a PNP bi-polar junction transistor, such as Part No. MMBT2907A, also manufactured by Motorola. Resistors 86, 88, 90, 92 and 94 have resistance values as shown in Table 2. The resistors are preferably implemented in thick film on a printed circuit board and have a 1% tolerance.

TABLE 2

| |
|---|
| Resistor 86 = 2.15 kΩ |
| Resistor 88 = 4.64 kΩ |
| Resistor 90 = 1.00 kΩ |
| Resistor 92 = 100 kΩ |
| Resistor 94 = 261 kΩ |

The operation of the gain block 60 shown in FIG. 6A will now be described. As the control button 30 is displaced from its neutral position toward the forward direction, the output of the low-pass filter 52, shown in FIG. 4, begins to increase from 4.0 volts DC. This output from the low-pass filter 52 becomes an input to the gain block 60 and is coupled to the emitters and bases of the transistors 82 and 84 as shown in FIG. 6A. When the input voltage is between approximately 4.0 volts and 4.7 volts, the transistors 82 and 84 are off and the voltage at the collectors of the transistors 82 and 84 stays fixed, as determined by the values of the resistors 90, 92 and 94. In the present embodiment, the chosen resistor values maintain the collector voltage at the level corresponding to 1/100th of the full speed, thereby creating the flat spot in the speed control curve.

The rotational speed that corresponds to the flat spot in the speed control curve may be adjusted by changing the resistance value of the resistor 92. For example, the fixed minimum speed will increase as the resistance of the resistor 92 is decreased.

Within the 30% to 80% range of control button 30 positions, the base-collector junction of either transistor 84 or transistor 82 turns on due to current flowing through the resistor 86. More specifically, when the control button 30 is located within the 30% to 87% range in the forward direction, the transistor 82 turns on, and when the control button 30 is located within the 30% to 87% range in the reverse direction, the transistor 84 turns on. For control button 30 positions within these ranges, the collector voltage varies almost linearly with the output of the low-pass filter 52.

At approximately the 87% point in the displacement of the control button 30, the transistor 82 or 84 becomes fully turned on. This causes a rapid increase to full speed with further control button 30 displacement. The point at which the transistors 82 and 84 become fully turned on is determined by the resistors 86 and 88. For example, by decreasing the resistance value of the resistor 86 with respect to the value of the resistor 88, the point at which the gain block output begins to quickly increase can be moved to the left in FIG. 5. Accordingly, the shape of the non-linear transformation performed by the circuit of FIG. 6A can be changed by varying the values of the resistors.

The 1/100th speed and the full speed as determined by the transfer characteristic 61 of the gain block 60 preferably are independent of temperature under normal operating conditions. As shown in FIG. 5, 1/100th speed and full speed for the gain block circuit of FIG. 6A are constant for temperatures of 0° C., 25° C. and 50° C.

An alternative embodiment of the gain block 60 is shown in FIG. 6B. The output of the low-pass filter 52 is provided to an analog-to-digital converter 96. The analog-to-digital converter 96 converts the analog output of the low-pass filter 52 into a digital signal. The digital signal from the analog-to-digital converter 96 is coupled to a memory module 98. The memory module 98 provides a predetermined output corresponding to the digital input. The predetermined output is coupled from the memory module 98 to a digital to analog converter 100, which is then coupled to the motor controller 62 shown in FIG. 3.

In the alternative embodiment, the memory module 98 may be an Erasable Programmable Read Only Memory ("EPROM") having 8 bit address and data lines, in which case the converters 96 and 100 will also be 8 bit converters. The memory module 98 is programmed to give a conversion, or look-up table, between the input digital value and the desired output digital value. For an 8 bit memory module, the input voltage range may be quantized into 256 discrete levels by the 8 bit analog-to-digital converter 96. The digital output of the analog-to-digital converter 96 drives the address lines of the EPROM. For each address input, there is a corresponding data output. For this embodiment, the amplifier/limiter 51 preferably produces an output between 0 volts and 5 volts, with 0 volts corresponding to the reverse travel limit of the control button 30 and 5.0 volts corresponding to the forward travel limit of the control button 30. By using a digital nonlinear gain block as shown in FIG. 6B, the shape of the nonlinear gain block can be tailored in accordance with the intended application by storing appropriate data in the EPROM.

Figure 7A:
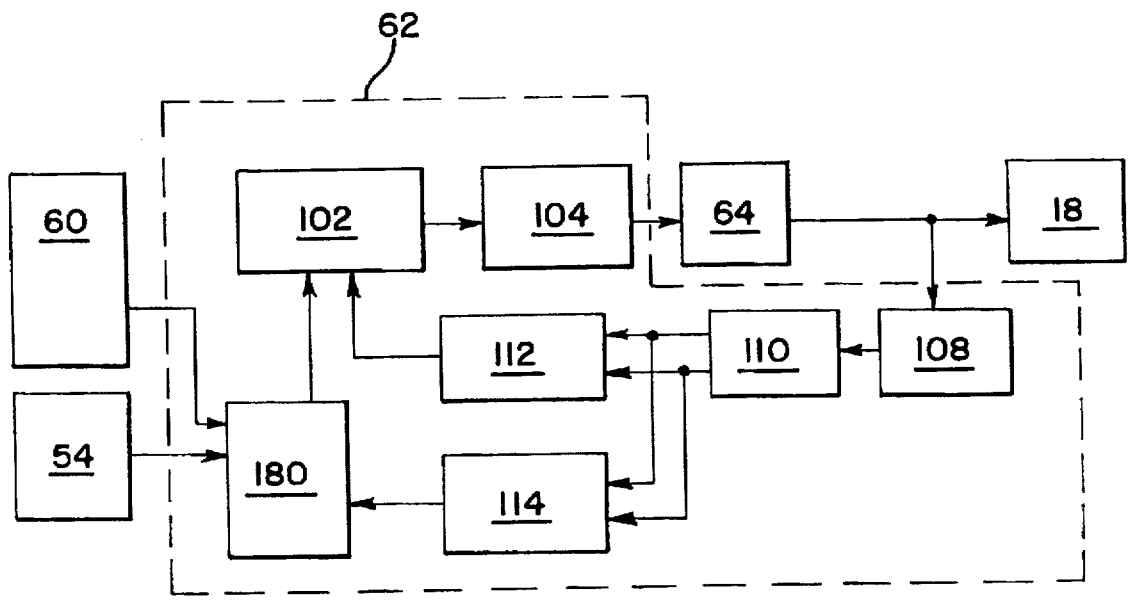
FIG. 7A is a block diagram of a preferred embodiment of the motor controller shown in FIG. 3.

FIG. 7A is a block diagram of a preferred embodiment of the motor controller 62 shown in FIG. 3. The output of the gain block 60 is coupled to a velocity servo 102. An output of the velocity servo 102 is coupled to a motor driver 104 which is in turn coupled to the motor 64. The motor 64, which is preferably a DC motor, has a shaft that is mechanically coupled to the ultrasound transducer 18.

An encoder 108 is coupled to the motor 64. The encoder 108 is preferably a quadrature encoder that is mounted to the shaft of the motor 64. The encoder 108 may be a standard two-channel quadrature encoder that produces a logic level transition at the rate of 16 transitions per motor shaft revolution. A DC motor and a quadrature encoder that are suitable for this application are available from MicroMo of St. Petersburg, Fla., Part Nos. 1331T-012S and HEM-1516-16, respectively.

As shown in FIG. 7A, an output from the encoder 108 may be provided to a detector 110. The detector 110 is coupled to a velocity detector 112, which is in turn coupled to the velocity servo 102.

The detector 110 may produce two output signals. A first output signal 111 represents the direction in which the motor shaft is turning, and a second output signal 113 being a train of pulses whose frequency represents the motor velocity. The velocity detector 112 converts the two signals 111 and 113 into a voltage that is proportional to the actual motor velocity and provides that voltage to the velocity servo 102.

During rotation of the ultrasound transducer 18, the velocity servo 102 compares the desired velocity, as represented by the output of the gain block 60, with the actual velocity, as represented by the output of the velocity detector 112. The velocity servo 102 amplifies any difference between the actual velocity and the desired velocity. This signal becomes the input to the motor driver 104. The motor driver 104 preferably operates in a linear voltage mode, i.e., a linear change in the output of the velocity servo 102 produces a linear change in the voltage applied to the motor 64.

The detector 110 may also be coupled to an up/down counter 114, as shown in FIG. 7A. The up/down counter 114 provides three signals to a motor disable circuit 180. The motor disable circuit 180 also receives the outputs of the deadband detector 54 and the gain block 60. The operation of the motor disable circuit is described below in reference to FIG. 10.

In a preferred mode of operation, the system is initialized by resetting the up/down counter 114 and rotating the ultrasound transducer 18 to its 0 degree position upon start up. In this manner, the up/down counter 114 keeps track of the position of the ultrasound transducer 18 with respect to its 0 degree position by monitoring the output of the detector 110. Preferably, a microprocessor 184, shown in FIG. 8, initializes the system.

Figure 7B:
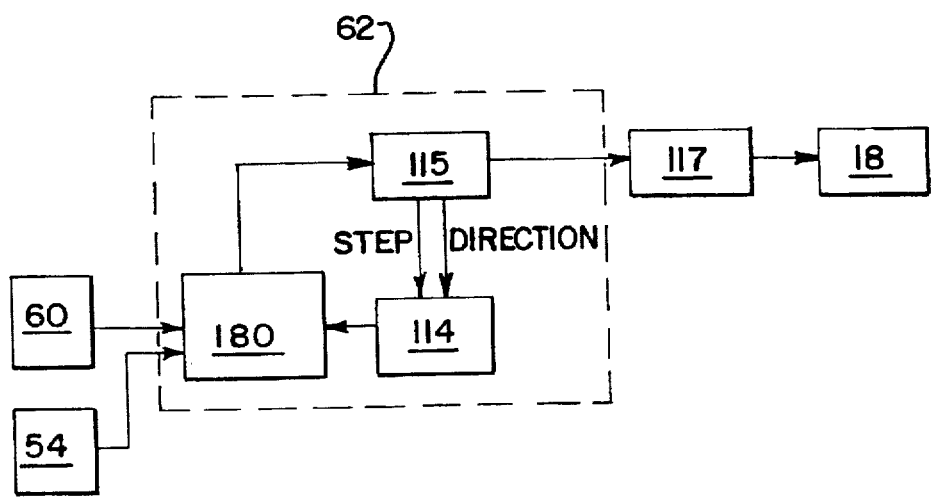
FIGS. 7B and 7C are block diagrams of alternative embodiments of the motor controller shown in FIG. 3.
Figure 7C:
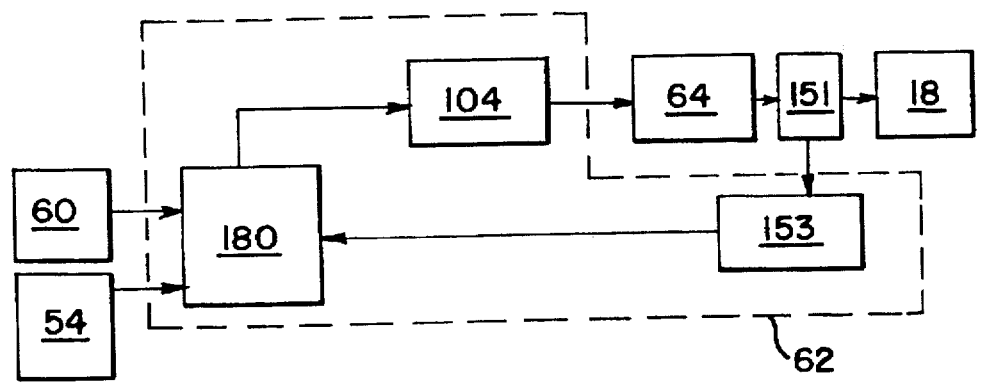

FIGS. 7B and 7C are block diagrams of alternative embodiments of the motor controller 62 shown in FIG. 3. In FIG. 7B, the motor controller 62 is a stepper motor driver 115 coupled to the up/down counter 114. The stepper motor driver 115 is also coupled to a stepper motor 117.

The stepper motor driver 115 provides both a step signal and a direction signal to the up/down counter 114, as shown in FIG. 7B. The up/down counter 114 generates a signal representing the position of the ultrasound transducer 18 from the step signal and the direction signal. The output of the up/down counter 114 is coupled to the motor disable circuit 180. The motor disable circuit 180 also receives inputs from the gain block 60 and the deadband detector 54. An output of the motor disable circuit 180 is coupled to the stepper motor driver 115. A disadvantage of the embodiment shown in FIG. 7B is that switching stepper motor noise may interfere with the ultrasound image.

FIG. 7C shows an alternative arrangement for controlling the position of the ultrasound transducer 18. A motor driver 104 is coupled to a DC motor 64. A gear box 151 couples the DC motor 64 to a ten-turn potentiometer 153. The gear box 151 provides gear reduction between the DC motor 64 and the potentiometer 153. The potentiometer 153 is coupled to the motor disable circuit 180, which also receives inputs from the gain block 60 and the deadband detector 54. The motor disable circuit 180 is coupled to the motor driver 104. A disadvantage of the embodiment of FIG. 7C is that the gear box 151 introduces backlash, which may create error in the potentiometer's ability to measure the position of the motor shaft. In addition, the potentiometer 153 is prone to early mechanical failure as compared to the encoder approach. The embodiment shown in FIG. 7A is, therefore, preferred.

Figure 8:
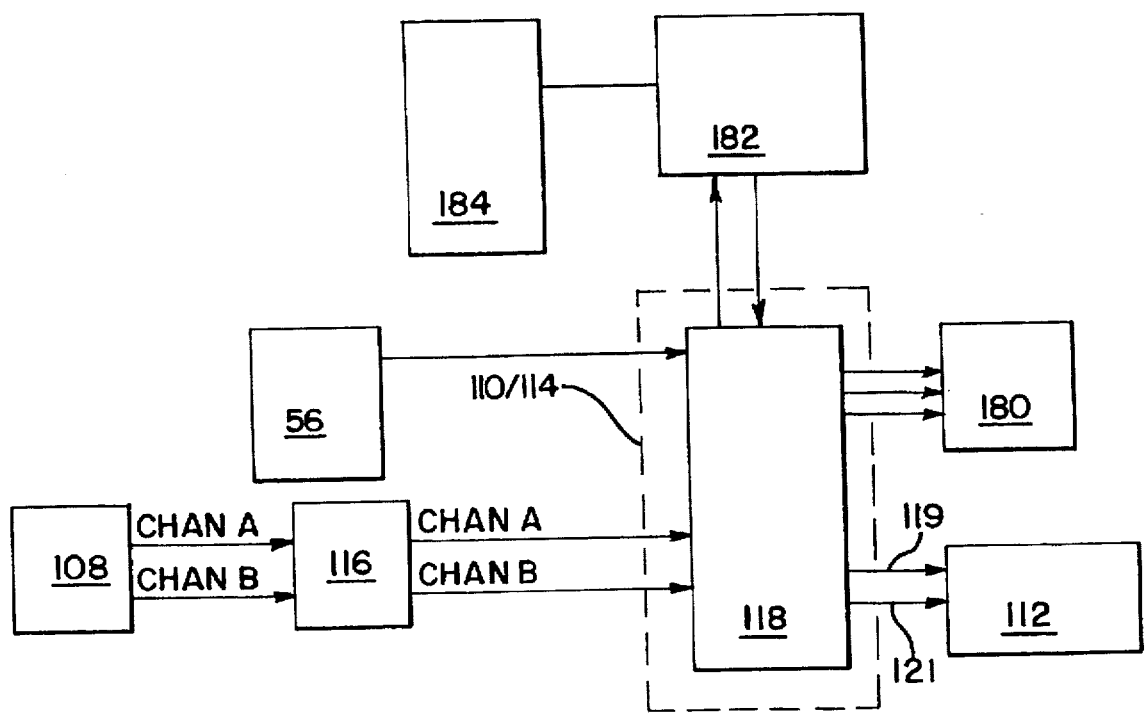
FIG. 8 is an electrical schematic of preferred embodiments of the detector and up/down counter shown in FIG. 7A.

FIG. 8 is an electrical schematic of preferred embodiments of the detector 110 and up/down counter 114 shown in FIG. 7A. As described above, the encoder 108 produces two logic level signals, which are shown in FIG. 8 as Channel A and Channel B. For each channel, the encoder 108 produces 16 encoder transitions per motor shaft revolution. As shown in FIG. 8, the signals Channel A and Channel B are coupled by logic buffers 116 to a field programmable gate array ("FPGA") 118. The FPGA 118 performs the functions of the detector 110 and up/down counter 114 shown in FIG. 7A. A commercially available FPGA that is suitable for this application is made and sold by XILINX, Inc. of San Jose, Calif., as Part No. XC4005A-5TQ144C.

The FPGA 118 generates a logic level signal 119 that indicates the direction in which the motor is moving and also generates a pulse train 121 having 64 pulses per motor shaft revolution. The FPGA 118 uses these two signals to control an internal up/down counter thereby keeping track of the motor position. The two signals generated by the FPGA 118 are also used externally to determine the motor velocity by coupling them to the velocity detector 112.

As shown in FIG. 8, the FPGA 118 preferably is in serial communication with a microprocessor 184 through a memory module 182. The memory module 182 is preferably a dual port 2 k by 8 bit random access memory. In the preferred mode of operation, the microprocessor 184 initializes the FPGA 118 by instructing the FPGA 118 to rotate the ultrasound transducer 18 to its home position and resetting the internal counter of the FPGA 118.

The FPGA 118 provides the advantage of monitoring the position of the ultrasound transducer 18 without the application of a system clock, which may generate electrical noise that interferes with imaging. The FPGA 118 is configured as a state-machine, keeping track of the ultrasound transducer 18 position, the motor 64 speed and end-of-travel limits without the need for a continuous clock. The system clock may then be applied to the FPGA 118 for a very short burst between ultrasound image frames for quick serial communication between the FPGA 118 and the microprocessor 184.

Figure 9A:
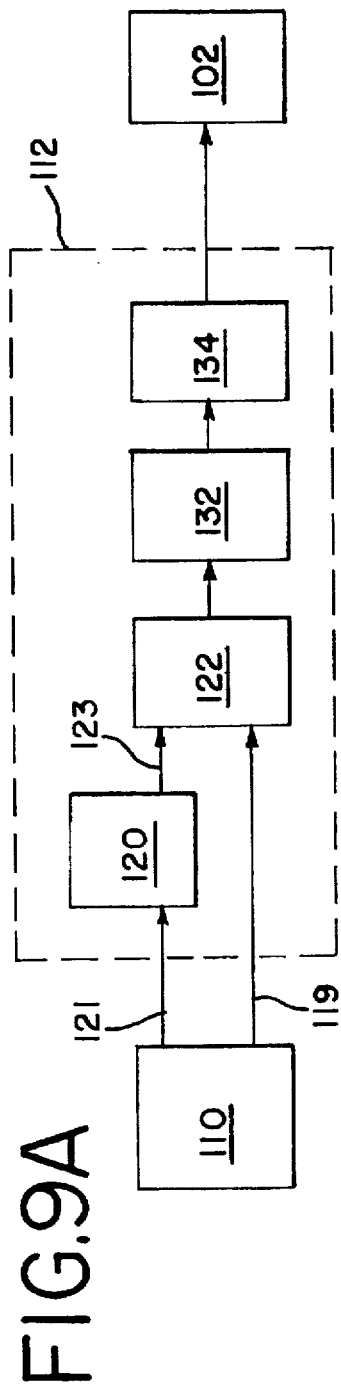

FIG. 9A and FIGS. 9B through 9F are a block diagram and an electrical schematic, respectively, of the velocity detector 112 and velocity servo 102 shown in FIG. 7A. As shown in FIG. 9A, the velocity detector 112 includes a one-shot converter circuit 120 that is coupled to the pulse train output 121 of the FPGA 118. The one-shot converter circuit 120 converts the variable width pulses of the FPGA output signal 121 into a signal having pulses with precisely controlled pulse width.

The output 123 of the one-shot converter circuit 120 and the encoder direction signal 119 generated by the FPGA 118 are provided as inputs to a velocity polarity restorer circuit 122, as shown in FIGS. 9A and 9C. The velocity polarity restorer circuit 122 operates to precisely control the amplitude of the pulse train, and produces a DC output corresponding to the average voltage of the pulse train.

Referring again to FIG. 9A, the output of the velocity polarity restorer circuit 122 is coupled to a velocity ripple filter 132, which removes ripple from the DC output of the velocity polarity restorer circuit 122. The velocity ripple filter 132 is coupled to a velocity sensor full-scale adjust circuit 134, which amplifies the output of the filter 132. The output of the velocity sensor full-scale adjust circuit 134 is coupled to the velocity servo 102.

Figure 9B:
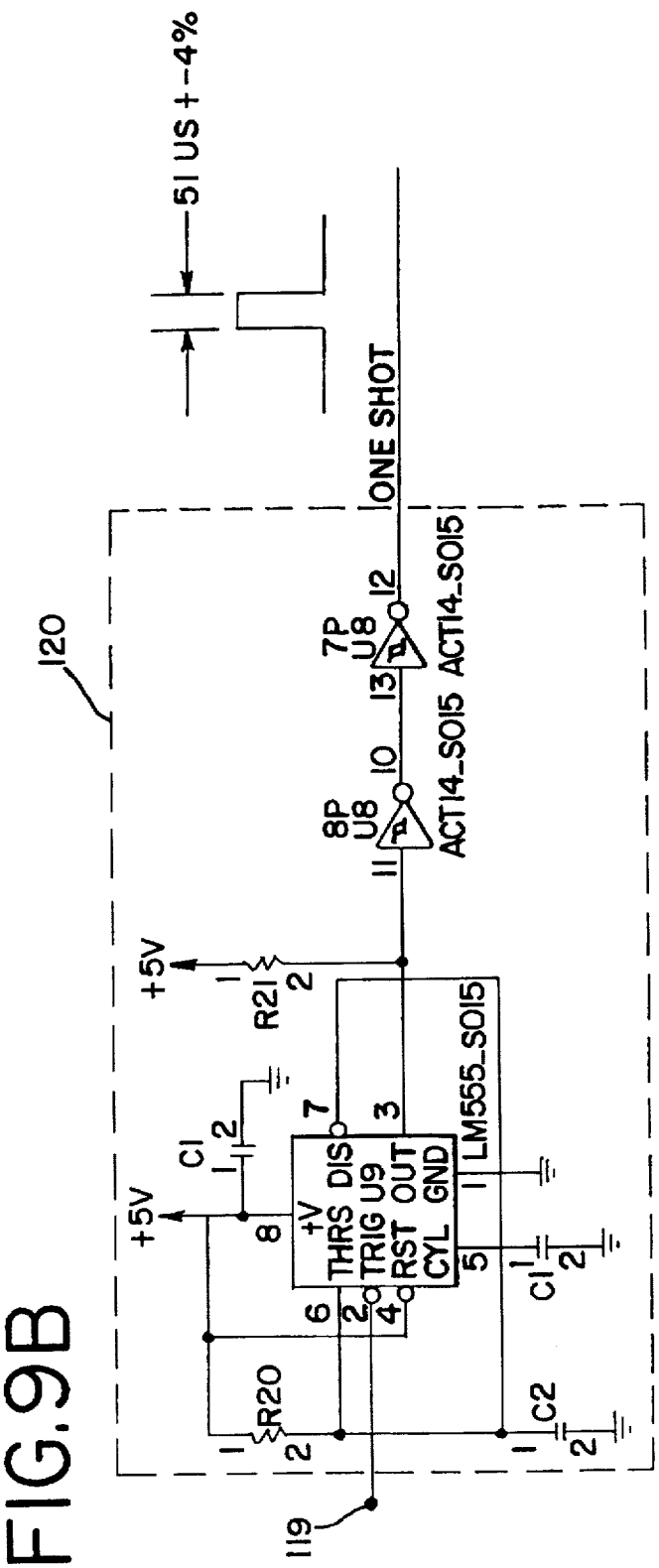

FIG. 9B is an electrical schematic of the one-shot converter circuit 120. The pulse train output 121 of the FPGA 118 is coupled to the trigger of one-shot converter 210. A one-shot converter 210 that is suitable for this application is available from National Semiconductor, Part No. LM555CM. The resistors, R20 and R21, and the capacitors, C1 and C2, have values as shown in Table 3. As shown in FIG. 9B, the one-shot converter circuit 120 produces, for each input pulse, an output pulse with a 51 microsecond pulse width.

FIG. 9C is an electrical schematic of the velocity polarity restorer circuit 122. As shown in FIG. 9C, the output signal 123 from the one-shot converter circuit 120 and the encoder direction signal 119 from the FPGA 118 are supplied as inputs to a multiplexer 124 in the velocity polarity restorer circuit 122. The output of the multiplexer 124 is a pulse train 125 in which the pulses have precise amplitude and width.

In the absence of a one-shot pulse, a switch S2-D2 of the multiplexer 124 in the velocity polarity restorer circuit 122 is opened. In this condition, the noninverting input to an operational amplifier 126 is held at 4.0 volts by a resistor 128 and a 4 volt reference voltage. When a pulse arrives, the switch S2-D2 of the multiplexer 124 is closed for the duration of the pulse causing the resistor 128 to be pulled toward 0 volts or 8 volts through the resistor 130, depending upon the state of the encoder direction signal 119. Component values for the resistors 128 and 130 and the capacitor C3 are provided in Table 3 below.

The average voltage of the precision amplitude precision width pulses at the output of the multiplexer 124 is proportional to the actual motor velocity. The velocity polarity restorer circuit 122 restores the sign of the velocity with reference to the 4 volt reference voltage in order to tell the difference between forward velocities and reverse velocities.

The DC output of the velocity polarity restorer circuit 122 is coupled to the velocity ripple filter 132. An electrical schematic of the velocity ripple filter is shown in FIG. 9D. At very slow speeds, encoder pulses in the train are coming infrequently, which causes unwanted ripple in the average DC voltage at the output of the velocity polarity restorer circuit 122. Accordingly, the velocity ripple filter 132, as shown in FIGS. 9A and 9B, removes the encoder ripple from the average DC level without substantially increasing time delay.

As shown in FIG. 9D, the velocity ripple filter 132 is preferably a three-pole Chebychev low-pass filter with 0.5 dB passband ripple and a cut-off frequency at 410 Hz. The output of the velocity polarity restorer circuit 122 is coupled through three resistors R22 to the noninverting input of an operational amplifier 127. The output of the operational amplifier 127 is coupled to the velocity sensor full-scale adjust circuit 134. Although a three-pole Bessel filter may alternatively be used to achieve less overshoot, the three-pole Chebychev filter provides a slight improvement in rise time and more stability in the feedback loop.

The velocity sensor full-scale adjust circuit 134 amplifies the output of the velocity ripple filter 132 so that a full-speed signal produces 6.5 volts if the motor is turning in the forward direction or 1.5 volts if the motor is turning in the reverse direction.

As shown in FIG. 9E, the output of the velocity ripple filter 132 is coupled to the noninverting input of an operational amplifier 129. The inverting input of the operational amplifier 129 is coupled through a resistor R25 to a 4 volt reference. A resistor R24 and a capacitor C8 are coupled between the output of the operational amplifier 129 and its inverting input. The output signal 136 of the velocity sensor full-scale adjust circuit 134 is a DC voltage level corresponding to the actual velocity of the motor 64. Component values for the resistors R24 and R25 and the capacitor C8 are provided below in Table 3.

FIG. 9F is an electrical schematic of the velocity servo 102. The output of the operational amplifier 129 is coupled through a resistor R26 to an operational amplifier 138. A capacitor C10 is coupled between the output of the operational amplifier 138 and its inverting input. The output of the operational amplifier 138 is also coupled through a resistor R27 and a capacitor C9 to the resistor R26. A 4 volt reference is coupled to the noninverting input of the operational amplifier 138 through a resistor R26. A capacitor C11 is coupled between the noninverting input and ground. Component values for the resistors R26 and R27 and the capacitors C9, C10 and C11 are provided below in Table 3. The operational amplifiers 126, 127, 129 and 138 are preferably Part No. LT1211CS8 from Linear Technology of Milpitas, Calif.

| | |
|---|---|
| R20 = 46.4kΩ, .1%, THN | C1 = 0.1 μF |
| R21 = 4.64kΩ, .1%, THK | C2 = 1.0nF COG 1% 50 v |
| R22 = 42.2kΩ, .1%, THN | C3 = 1.0nF COG 1% 50 v |
| R23 = 121kΩ, .1%, THN | C4 = 22nF X7R 10% 50 v |
| R24 = 16.2kΩ, .1%, THN | C5 = 100nF X7R 10% 50 v |
| R25 = 10kΩ, .1%, THN | C6 = 820pF COG 5% 100 v |
| R26 = 10kΩ, .1%, THN | C7 = 100pF COG 5% 100 v |
| R27 = 31.6kΩ, .1%, THN | C8 = 100pF COG 1% 100 v |
| C9 = | 820nF X7R 10% 50 v |
| Resistor 128 = 10.0kΩ, .1%, THN | C10 = 22nF X7R 10% 50 v |
| Resistor 130 = 6.19kΩ, .1%, THN | C11 = 1.0nF COG 1% 50 v |

The velocity servo 102 compares the actual velocity of the motor 64, as represented by the output of 136 of the full-scale adjust circuit 134, with a desired motor velocity, as represented by a signal 188 provided by the motor disable circuit 180. The operational amplifier 138 generates a output signal 144 representing the integrated difference between the actual velocity signal 136 and the desired velocity signal 188. The output signal 144 is coupled to the motor driver 104, shown in FIGS. 7A and 11, which directly controls the motor velocity.

Figure 10:
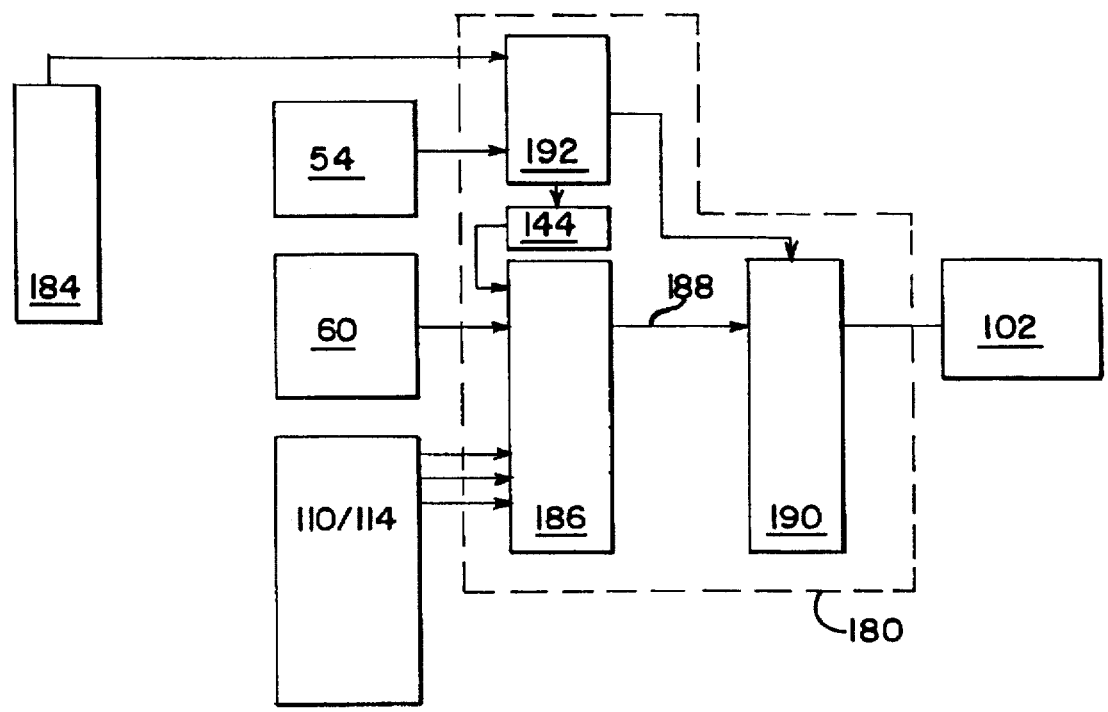
FIG. 10 is a schematic of the motor disable circuit shown in FIG. 7A.

FIG. 10 is an electrical schematic of the motor disable circuit 180 shown in FIG. 7A. The detector and up/down counter 110/114 and the gain block 60 are coupled to a multiplexer 186. A remote speed-setting circuit 194 is also coupled to the multiplexer 186. The deadband detector 54 and the microprocessor 184 are coupled to a second multiplexer 192. The multiplexer 192 is coupled to the remote speed-setting circuit 194 and a switch 190. The switch 190 is coupled to the velocity servo 102.

In operation, the multiplexer 186 selects the desired velocity from either the gain block 60 or the remote speed-setting circuit 194 in accordance with the three velocity bits, which form a speed selection signal, provided by the up/down counter 114 of the FPGA 118. When the probe 10 is used in the manual mode by moving the control button 30, as indicated by the speed selection signal, the multiplexer 186 selects the desired velocity signal from the gain block 60.

On the other hand, when the speed selection signal from the up/down counter 114 of the FPGA 118 indicates that the probe 10 is to operate in the remote mode, the multiplexer 186 selects one of several predetermined velocities from the remote speed-setting circuit 194 in accordance with the speed selection signal. When the probe 10 operates in a remote mode, the microprocessor 184 provides a direction selection signal to the second multiplexer 192. The multiplexer 192 responds to the direction selection signal by coupling an appropriate reference voltage, 8.0 volts for forward and 0 volts for reverse, to the speed-setting circuit 194. The desired velocity signal is then selected by the multiplexer 186 from the speed-setting circuit 194 and is provided to the switch 190 on the signal line 188.

In a preferred embodiment for remote operation, the desired velocity on the signal line 188 may be set to zero or one of six fixed speeds in either the forward or reverse direction. The multiplexer 186 is provided with eight selectable inputs: one for each of the six fixed speeds, zero and the manual input from the gain block 60. The multiplexer 186 then selects the desired input in accordance with the three velocity bits from the up/down counter 114 of the FPGA 118.

The six fixed speeds may be provided by the remote speed-setting circuit 194 to the multiplexer 186 as follows. The remote speed-setting circuit 194 is formed by connecting a first end of six resistors, R28, R29, R30, R31, R32 and R33, to a common node. The common node may be coupled through the multiplexer 192 to either the 8.0 volt reference or the 0 volt reference. The values of the resistors, and the corresponding speeds as a fraction of full speed, are provided below in Table 4. A second end of each resistor, R28 through R33, is coupled to a separate selectable input of the multiplexer 186.

While the speed of the motor is determined by the value of the resistor R28 through R33 in the speed-setting circuit when in the remote mode, the direction is determined by the microprocessor 184. When the microprocessor 184 provides a signal to the multiplexer 192 indicating that the ultrasound transducer 18 is to rotate in the forward direction, the multiplexer 192 couples the 8.0 volt reference to the common node. On the other hand, when the microprocessor 184 provides a signal to the multiplexer 192 indicating that the ultrasound transducer 18 is to rotate in the reverse direction, the multiplexer 192 couples the common node to ground.

TABLE 4

| |
|---|
| R28 = 147kΩ, .1%, THN, 1/10 speed |
| R29 = 121kΩ, .1%, THN, 1/8 speed |
| R30 = 56.2kΩ, .1%, THN, 1/4 speed |
| R31 = 21.5kΩ, .1%, THN, 1/2 speed |
| R32 = 11.0kΩ, .1%, THN, 3/4 speed |
| R33 = 6.19kΩ, .1%, THN, full speed |

The selected resistor from the remote speed-setting circuit 194 forms a voltage divider with the resistor R26, shown in FIG. 9F, that is coupled between the noninverting input of the operational amplifier 138 and the 4 volt reference. The speed corresponding to each resistor, R28 through R33, is provided above in Table 4. When no resistor is selected by the multiplexer 186, the 4 volt reference, which corresponds to zero velocity, is applied to the operational amplifier 138 as the desired velocity.

The second multiplexer 192 controls the state of the switch 190 in accordance with the inputs from the deadband detector 54 and the microprocessor 184. If, for example, the deadband detector 54 indicates that the control button 30 is positioned within the ±14% deadband zone, then the switch 190 remains open and the desired velocity on the signal line 188 is not provided to the velocity servo 102.

Preferably, the switch 190 couples the signal 188 to the operational amplifier 138 of the velocity servo 102 whenever the motor 64 is supposed to be moving. Conversely, the switch 190 preferably blocks the signal 188 when the control button 30 is in its neutral position, when the ultrasound transducer 18 reaches its end-of-travel limits, or when a stalled motor 64 is detected. As noted above, the state of the switch 190 is controlled by second multiplexer 192 of the motor disable circuit 180, as shown in FIG. 10.

During use of the probe 10, the operational amplifier 138 compares the desired velocity signal 188, which derives from the position of the control button 30, to an actual velocity signal 136, which derives from the encoder 108, to control rotation of the ultrasound transducer 18. In order to improve the performance of the motor controller, it is, therefore, desirable that the time delay in the path of the actual velocity signal 136 be minimized. The embodiments of the elements in the feedback path of the actual velocity signal, as shown in FIGS. 8 and 9, reflect this design consideration.

The accuracy of the motor speed control described herein depends primarily upon the tolerances of the resistors in Table 4, the tolerance of the resistor R26, the accuracy of the voltage references and the one-shot pulse width. The circuitry described herein provides accuracy to within approximately ±5%, independent of the friction on the motor 64.

Figure 11:
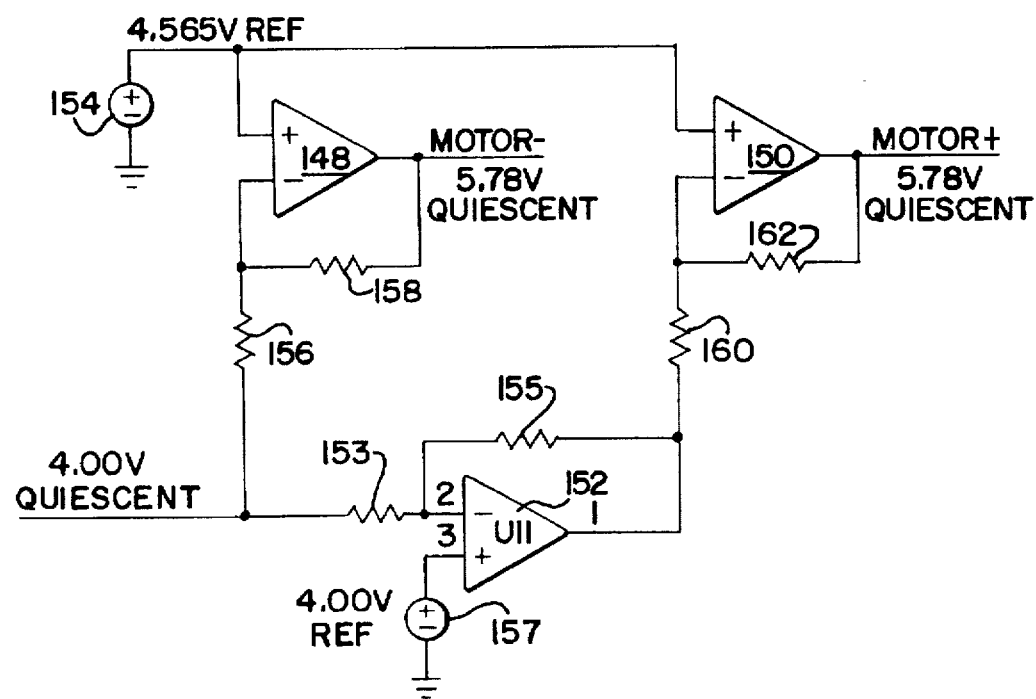
FIG. 11 is an electrical schematic of the motor driver shown in FIG. 7A.

FIG. 11 is an electrical schematic of the motor driver 104 shown in FIG. 7A. The motor driver 104 includes two power operational amplifiers 148 and 150 and an inverter 152. A 4.565 volt DC reference 154 is coupled to the noninverting inputs of the power operational amplifiers 148 and 150. The inverter 152 includes an input resistor 153 and a feedback resistor 155, which have the same resistance value of 10 kΩ, and therefore produce unity gain. The noninverting input of the inverter 152 is coupled to a 4.0 volt DC reference 157.

The signal 144 is coupled to the inverting input of the power operational amplifier 148 through a resistor 156. A feedback resistor 158 is connected between the output of the power operational amplifier 148 and its inverting input. The resistor 156 is 10 kΩ and the resistor 158 is 21.5 kΩ. The gain of the power operational amplifier 148, which is determined by the ratio of the resistances of the feedback resistor 158 with respect to the resistor 156, is 2.15. The output of the power operational amplifier 148 is coupled to the negative terminal of the motor 64.

As shown in FIG. 11, the signal 144 is also coupled to the inverting input of the power operational amplifier 150 through the inverter 152 and a resistor 160. A feedback resistor 162 is connected between the output of the power operational amplifier 150 and its inverting input. The resistor 160 is 10 kΩ and the resistor 162 is 21.5 kΩ. The gain of the power operational amplifier 150, which is determined by the ratio of the resistances of the feedback resistor 162 with respect to the resistor 160, is 2.15. The output of the power operational amplifier 150 is coupled to the positive terminal of the motor 64.

Figure 12:
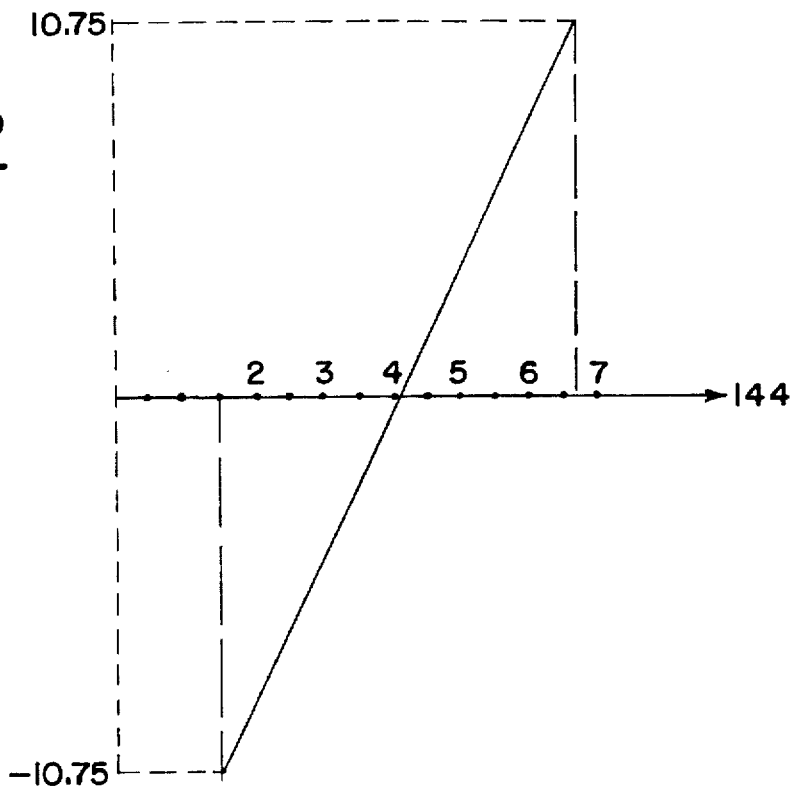
FIG. 12 is a graph showing the input signal voltage level versus the net voltage applied to the motor for the motor driver shown in FIG. 11.

In operation, the motor driver 104 responds to the input signal 144 as shown in FIG. 12, which is a graph of the input signal 144 voltage level versus the net voltage applied to the motor 64 for the motor driver 104 shown in FIG. 11. The net voltage applied to the motor 64 is the difference between the output of the power operational amplifier 150 and the output of the power operational amplifier 148.

When the input signal 144 is 4.0 volts, the outputs of the power operational amplifiers 148 and 150 are the same, 5.78 volts. Because the positive and negative terminals of the motor 64 are at the same voltage, the net voltage applied to the motor 64 is zero and the motor 64 does not rotate. As the voltage of the input signal 144 increases from 4.0 volts, the output of the power operational amplifier 150 increases from 5.78 volts and the output of the power operational amplifier 148 decreases from 5.78 volts. The net positive voltage causes the motor 64 to rotate in the forward direction at a speed proportional to the net voltage. Similarly, as the voltage of the input signal 144 decreases from 4.0 volts, the output of the power operational amplifier 150 decreases from 5.78 volts and the output of the power operational amplifier 148 increases from 5.78 volts. The net negative voltage causes the motor 64 to rotate in the reverse direction at a speed proportional to the net voltage.

For the motor driver 104 shown in FIG. 11, the net voltage applied to the motor 64 is 4.3 times the difference between the input signal 144 and 4.0 volts. A linear change in the signal 144 produces a linear change in the net voltage applied to the motor 64. The power operational amplifiers 148 and 150 may be operated from an 11.5 volt source so that 5.78 volts is the approximate midpoint of the operational voltage range.

Figure 13:
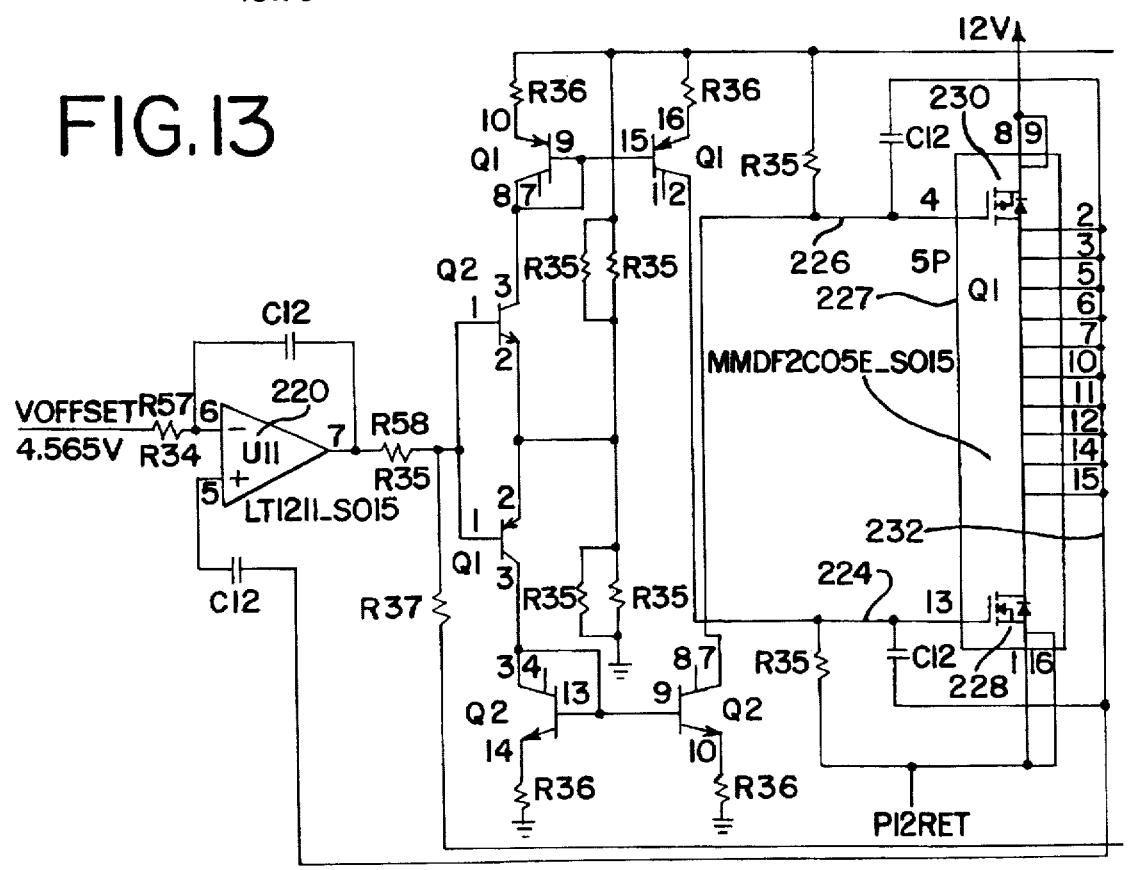
FIG. 13 is an electrical schematic of a power operational amplifier from the motor driver shown in FIG. 11.

FIG. 13 is an electrical schematic of the power operational amplifiers 148 and 150 shown in FIG. 11. The 4.565 volt reference 154 is coupled through a resistor R34 to the inverting input of an operational amplifier 220. The output of the operational amplifier 220 is coupled by a resistor R35 to a transistor driver stage 222. The transistor driver stage 222 supplies gate driver signals 224 and 226 to a power stage 227 containing a pair of MOSFETs 228 and 230, respectively. The output 232 of the power operational amplifier 148 is coupled to the negative terminal of the motor 64, whereas, for the power operational amplifier 150, the output 232 is coupled to the positive terminal of the motor 64. Component values for the electrical schematic of FIG. 13 are provided in Table 5 below. The operational amplifier 220 is preferably Part No. LT1211CS8 from Linear Technology of Milpitas, Calif.

The power stage 227 is preferably Part No. SI9950DY from Siliconix in Santa Clara, Calif., in which the MOSFET 230 is a p-channel device and the MOSFET 228 is an n-channel device. The transistors Q1 in FIG. 13 are PNP bipolar junction transistors, such as Part No. MMBT2907A manufactured by Motorola of Phoenix, Ariz. The transistors Q2 are NPN bipolar junction transistors, such as Part No. MMBT2222A, also manufactured by Motorola.

TABLE 5

R34 = 10.0kΩ, 1%, THK
R35 = 1kΩ, 1%, THK
R36 = 100Ω, 1%, THK
R37 = 4.99kΩ, .1%, THN
C12 = 1.0nF COG 1% 50 v

The amplifier/limiter 51, shown in FIG. 4, is preferably located on a printed circuit board within the control housing 12. The other circuitry described above is preferably located on printed circuit boards within the connector 22.

In a preferred embodiment of the invention, the ultrasound probe 10 may be operated in either a manual mode or a remote mode. When operated in the manual mode, the motor disable circuit 180 supplies the output of the gain block 60 as the desired velocity signal 188 to the velocity servo 102, unless the deadband detector 54 indicates that the actuator 28 is positioned within the ±14% deadband. If, in the manual mode, the deadband detector 54 indicates that the actuator 28 is positioned within the ±14% deadband, then the desired velocity signal 188 is forced to 4.0 volts (motor off), and the motor 64 is turned off.

When operated in the remote mode, the microprocessor 184 provides the FPGA 118 with information, such as when it should stop the motor 64 or change its speed. In addition, by communicating with the motor disable circuit 180, the microprocessor 184 is capable of starting motor 64 movement at a predetermined speed and direction. After being started by the microprocessor 184, motor control falls to the FPGA 118 and the microprocessor 184 preferably is turned off. It is the combination of the microprocessor 184 and the FPGA 118 that allows interference-free imaging in the remote mode.

Preferably, the ultrasound probe 10 may be operated in two distinct remote modes. In a first remote mode, the ultrasound transducer 18 is rotated at a selectable fixed speed. Images may be acquired during this rotation. The first remote mode is referred to herein as "remote velocity mode." In a second remote mode, the ultrasound transducer is quickly and accurately stepped from one position to another. Image data is acquired between steps. The second remote mode is referred to herein as "remote position mode."

In remote velocity mode, the microprocessor 184 communicates with the motor disable circuit 180 to initiate movement in a desired direction and at a desired speed. The microprocessor 184 also communicates with the FPGA 118. The multiplexer 186 from the motor disable circuit selects the desired fixed speed in accordance with the three velocity bits provided by the FPGA 118 to the multiplexer 186.

In remote position mode, it is desirable to move the ultrasound transducer 18 from one position to another as quickly and as accurately as possible. In accordance with the present invention, the following algorithm may be applied.

First, the microprocessor 184 sets up the final target position and a preliminary target position, such as a position 0.5° before the final target position, in the registers of the FPGA 118. The microprocessor 184 is then shut off. The FPGA 118 sets its three velocity bits to full speed causing the full positive 10.75 motor supply volts to be applied to the motor 64 to accelerate the motor 64 to its maximum velocity (full speed in the desired direction).

When the up/down counter 114 of the FPGA 118 determines that the motor 64 has reached the preliminary target position, the FPGA 118 sets its three velocity bits to reduce the motor speed to ½ speed. When the up/down counter 114 of the FPGA determines that the target position is reached, the FPGA 118 resets its three velocity bits to zero speed and the full negative −10.75 motor supply voltage is applied to dynamically break the motor 64. When the actual velocity decays to 1/20 full speed, the motor supply voltage is forced to zero (off).

When travelling at ½ speed, the dynamic breaking time for the present invention is approximately 4 milliseconds. This results in a very small target overshoot, approximately 0.1°. Although it is possible to subtract this observed overshoot from the target position to compensate for the overshoot, other factors may swamp out the correction. For example, changes in system friction, motor inertia, motor armature resistance, and recoil in the coupling between the motor 64 and the ultrasound transducer 18 may further degrade the accuracy of the target position by up to an additional ±0.3°. The motor 64 may, alternatively, be subjected to dynamic breaking from full speed, however, the resulting overshoot is then larger.

In accordance with the present invention, alternative speeds may be selected by the FPGA 118. For example, where it is not necessary to reach the target position as quickly as possible, the motor 64 may be run at a constant speed that is lower than the full speed, or the motor 64 may be run at full speed for a shorter period of time and then stepped in two or more steps to zero.

In addition, repetitive steps may be taken in the remote position mode, and it is not necessary that each step be of equal distance. The size of each step may be independently determined by the microprocessor 184 and the FPGA 118. Moreover, it is envisioned that more or fewer speeds may be used than the six fixed speeds described above.

In accordance with the present invention, the probe 10 may be automatically controlled to capture data for three-dimensional cardiology and radiology imaging applications, as described above with respect to the remote modes of operation. For example, in the remote position mode, the probe 10 may capture data from rapidly moving objects, such as a beating heart. The ultrasound transducer 18 may be quickly stepped to a target position, stopped to allow image data to be captured, and then quickly stepped to another target position, where additional data is captured. By stepping quickly to the required target positions, data required for three-dimensional reconstructions may be quickly obtained. As a further example, the probe 10 may be used in remote velocity mode in radiology applications, such as imaging the liver. In this mode, the ultrasound transducer 18 is rotated at a constant rate while capturing image data. The image data may be reconstructed into a three-dimensional image.

It is intended that the foregoing detailed description be regarded as illustrative rather than limiting, and it is understood that the following claims, including all equivalents, are intended to define the scope of the invention.

I claim:

1. In a probe having an ultrasound transducer that is mounted for rotation with respect to a plurality of scanplanes in a body and an actuator that includes structure that may be manually positioned within a range of positions, an apparatus for controlling rotation of the ultrasound transducer to a selected scanplane, said apparatus comprising:

a motor;

a motor controller coupled to the motor; and a gain block coupled between the actuator and the motor controller, the gain block having a continuous transfer characteristic and producing, for each position of the actuator, a signal representing a desired rotational velocity of the transducer.

2. An apparatus as claimed in claim 1, wherein the gain block has a nonlinear continuous transfer characteristic.

3. An apparatus as claimed in claim 2, wherein the gain block continuous transfer characteristic comprises:

a first region in which the desired velocity is fixed at a low velocity;

a second region continuous to the first region, wherein the desired velocity increases in an approximately linear manner; and a third region continuous to the second region, wherein the desired velocity increases more rapidly than in the second region to a maximum velocity.

4. An apparatus as claimed in claim 3, wherein the gain block provides a maximum velocity that is within the range of approximately 50 to 100 times the low velocity.

5. An apparatus as claimed in claim 3, further comprising an inhibitor for inhibiting movement of the ultrasound transducer, wherein the inhibitor is responsive to the actuator.

6. An apparatus as claimed in claim 5, wherein the inhibitor comprises a deadband detector.

7. An apparatus as claimed in claim 5 wherein the motor controller is coupled to the inhibitor and the gain block.

8. An apparatus as claimed in claim 7, wherein the motor controller is responsive to the inhibitor over a first range of actuator positions, and the controller is responsive to the gain block over a second range of actuator positions.

9. An apparatus for controlling rotation of an ultrasound transducer mounted within a distal portion of a probe and operatively associated with a bidirectional switch, the apparatus and the transducer comprising:

a motor mechanically coupled to the transducer; and a nonlinear gain block electrically coupled between the switch and the motor, wherein the nonlinear gain block receives a first signal from the switch and transmits a second signal to the motor in order to provide for the rotation of the ultrasound transducer to a selected scanplane.

10. An apparatus as claimed in claim 9, further comprising a sensing element for sensing displacement of the bidirectional switch.

11. An apparatus as claimed in claim 10, further comprising an inhibitor for inhibiting the rotation of the transducer until the bidirectional switch is displaced by a predetermined amount.

12. An apparatus as claimed in claim 9, further comprising:

a third signal generator for generating a third signal corresponding to an actual motor velocity; and a comparator for comparing the third signal to the second signal.

13. An apparatus as claimed in claim 12, wherein the the third signal generator comprises:

a magnetic quadrature encoder coupled to the motor; and a quadrature detector coupled to the encoder.

14. An apparatus as claimed in claim 13, wherein the third signal generator further comprises a polarity restorer coupled to the detector.

15. An apparatus as claimed in claim 14, wherein the third signal generator further comprises a ripple filter coupled to the polarity restorer.

16. An apparatus as claimed in claim 13, wherein the third signal generator further comprises a precision one-shot circuit coupled to the quadrature detector.

17. An apparatus as claimed in claim 13, wherein the quadrature detector comprises a field programmable gate array.

18. An apparatus as claimed in claim 12, further comprising an adjustor for adjusting the actual motor velocity in accordance with a difference between the third signal and the second signal.

19. An apparatus as claimed in claim 9, wherein the gain block produces a second signal that remains constant for a predetermined range of variation of the first signal.

20. An apparatus as claimed in claim 19, wherein the gain block produces a constant second signal that corresponds to a low motor velocity.

21. A probe having a control housing coupled to a transducer housing, which transducer housing contains an ultrasound transducer that is rotatably mounted for scanning a plurality of planes in a body, and a control button mounted to the control housing, comprising:

a first signal generator, the first signal representing a position of the control button;

a transforming element, the transforming element transforming the first signal into a second signal representing a desired velocity, the second signal having a nonlinear relation to the first signal;

a motor coupled to the transforming element, the motor coupled to the transducer in order to provide for rotation of the transducer; and a third signal generator, the third signal generator representing an actual motor velocity, said third signal generator being coupled to the motor.

22. A probe as claimed in claim 21, further comprising a motor controller coupled between the transforming element and the motor.

23. A probe as claimed in claim 22, wherein the third signal generator is electrically coupled to the motor controller.

24. A probe as claimed in claim 23, wherein the motor controller generates a fourth signal representing a difference between the second signal and the third signal.

25. A probe as claimed in claim 22, further comprising an inhibitor that inhibits movement of the ultrasound transducer, wherein the inhibitor is coupled between the first signal generator and the motor controller.

26. A probe as claimed in claim 21, wherein the third signal generator comprises an encoder connected to the motor.

27. A probe as claimed in claim 26, wherein the third signal generator further comprises a detector coupled to the encoder.

28. A probe as claimed in claim 27, wherein the third signal generator further comprises a restoring element for restoring polarity to the third signal.

29. A probe as claimed in claim 28, wherein the third signal generator further comprises a filtering element for filtering ripple from the third signal.

30. A probe as claimed in claim 29, wherein the filtering element comprises a low pass filter.

31. A method of controlling rotation of an ultrasound transducer to a selected scanplane, the ultrasound transducer being housed within a distal end of a probe having a user-operable actuator that is movable over a continuous range of positions, the method comprising the steps of;

generating a first signal representing the position of the actuator;

transforming the first signal into a second signal representing a desired velocity, wherein the second signal is a nonlinear transform of the first signal; and rotating the ultrasound transducer in accordance with the second signal.

32. A method as claimed in claim 31, further comprising the steps of:

generating a third signal representing an actual velocity of the ultrasound transducer; and comparing the third signal to the second signal.

33. A method as claimed in claim 32, further comprising the step of adjusting the actual velocity of the ultrasound transducer in accordance with the comparison.

34. A method as claimed in claim 31, further comprising the step of producing a signal representing a position of the rotating ultrasound transducer.

35. A method as claimed in claim 31, further comprising the step of inhibiting rotation of the ultrasound transducer when the actuator is located within a first predetermined portion of the continuous range.

36. A method as claimed in claim 35, wherein the second signal corresponds to a minimum speed when the actuator is located within a second predetermined portion and a third predetermined portion of the continuous range, said first predetermined portion separating the second and third predetermined portions of the continuous range.

* * * * *

UNITED STATES PATENT AND TRADEMARK OFFICE
CERTIFICATE OF CORRECTION

PATENT NO. : 5,720,285
DATED : February 24, 1998
INVENTOR(S) : Alan W. Petersen

It is certified that error appears in the above-identified patent and that said Letters Patent is hereby corrected as shown below:

<u>On the Title Page</u>

In column 1, after line 4, under "U.S. PATENT DOCUMENTS", insert the following line:

--5,402,793    4/1995    Gruner et al.    128/660--.

In column 1, line 8, after "1995" insert --(now abandoned)--.

In column 13, line 25, replace "C11" with --C11-- (bold) to be consistent with part designations.

In column 13, before line 30, insert the following title, --TABLE 3--, as a new line.

In column 13, line 38, fix "C9 = 820nF X7R 10% 50v" to conform to same form in chart.

In column 13, line 47, replace "a" with --an--.

Signed and Sealed this

Twenty-first Day of December, 1999

Attest:

Attesting Officer

Q. TODD DICKINSON

Acting Commissioner of Patents and Trademarks